United States Patent [19]

Takaya et al.

[11] Patent Number: 4,609,730
[45] Date of Patent: * Sep. 2, 1986

[54] 7-[SUBSTITUTED IMINO-2-(2-AMINOTHIAZOL-4-YL)-ACETAMIDO]-3(2,2-DIHALOVINYL OR ETHYNYL)-3-CEPHEM-4-CARBOXYLIC ACID (SYN ISOMERS), HAVING ANTIMICROBIAL ACTIVITIES

[75] Inventors: Takao Takaya, Kawanishi; Takashi Masugi, Ikeda; Kohji Kawabata, Osaka, all of Japan

[73] Assignee: Fujisawa Pharmaceutical Co., Ltd., Osaka, Japan

[*] Notice: The portion of the term of this patent subsequent to Aug. 7, 2001 has been disclaimed.

[21] Appl. No.: 552,065

[22] Filed: Nov. 15, 1983

[30] Foreign Application Priority Data

Nov. 22, 1982 [GB] United Kingdom ............... 8233215

[51] Int. Cl.$^4$ ............... C07D 501/22; A61K 31/545
[52] U.S. Cl. ............................ 514/202; 540/222
[58] Field of Search ............... 544/22, 27; 424/246; 514/226

[56] References Cited

U.S. PATENT DOCUMENTS

| | | | |
|---|---|---|---|
| 4,264,597 | 4/1981 | Hashimoto et al. | 544/16 |
| 4,307,230 | 12/1981 | Faye et al. | 544/22 |
| 4,342,760 | 8/1982 | Hashimoto et al. | 544/22 |
| 4,464,369 | 8/1984 | Takaya et al. | 544/22 |
| 4,492,694 | 1/1985 | Blaszczak et al. | 544/22 |

FOREIGN PATENT DOCUMENTS

| | | | |
|---|---|---|---|
| 53538 | 6/1982 | European Pat. Off. | 544/22 |
| 88385 | 9/1983 | European Pat. Off. | 544/22 |
| 2127812 | 8/1983 | United Kingdom | 544/22 |

OTHER PUBLICATIONS

Berger et al, Chem. Abst. 97:162691f.
Berger et al, Chem. Abst. 97:162696m, 162697n.
Faye et al, Chem. Abst. 97:162694j.

Primary Examiner—Donald G. Daus
Assistant Examiner—Cecilia Shen
Attorney, Agent, or Firm—Oblon, Fisher, Spivak, McClelland & Maier

[57] ABSTRACT

The invention relates to novel cephem compounds of high antimicrobial activity of the formula:

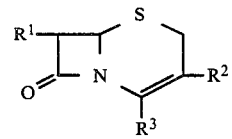

wherein
$R^1$ is amino, lower alkanoylamino, ar(lower)alkanoylamino, amino- or alkanoylaminothiazolyl(lower)alkanoylamino having a lower alkoxyimino, amino- or alkanoylaminothiazolyl(lower)alkanoylamino an ar(lower)alkoxycarbonyl(lower)alkoxyamino, aminothiazolyl(lower)alkanoylamino having a carboxy(lower)alkoxyamino, or aminothiadiazolyl(lower)alkanoylamino having a lower alkoxyimino,
$R^2$ is 2,2,-dihalovinyl or ethynyl, and
$R^3$ is carboxy or protected carboxy, and
pharmaceutically acceptable salts thereof.

17 Claims, No Drawings

7-[SUBSTITUTED IMINO-2-(2-AMINOTHIAZOL-4-YL)-ACETAMIDO]-3(2,2-DIHALOVINYL OR ETHYNYL)-3-CEPHEM-4-CARBOXYLIC ACID (SYN ISOMERS), HAVING ANTIMICROBIAL ACTIVITIES

The present invention relates to new cephem compounds and pharmaceutically acceptable salts thereof. More particularly, it relates to new cephem compounds and pharmaceutically acceptable salts thereof, which have antimicrobial activities, to processes for preparation thereof, to pharmaceutical composition comprising the same, and to a method of using the same therapeutically for the treatment of infectious diseases in human being and animals.

Accordingly, it is one object of the present invention to provide new cephem compounds and pharmaceutically acceptable salts thereof, which are highly active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula (I):

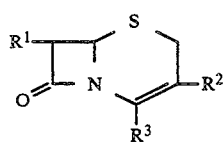

(I)

wherein
$R^1$ is amino or acylamino,
$R^2$ is 2,2-dihalovinyl or ethynyl, and
$R^3$ is carboxy or protected carboxy.

According to the present invention, the new cephem compounds (I) can be prepared by various processes which are illustrated in the following schemes.

Process 1

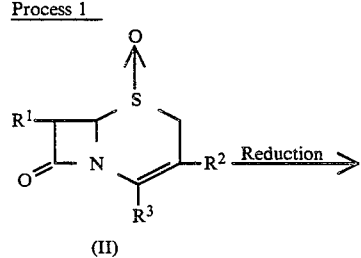

(II)
or a salt thereof $\xrightarrow{\text{Reduction}}$

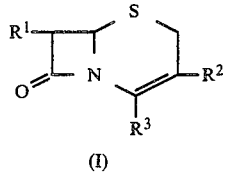

(I)
or a salt thereof

Process 2

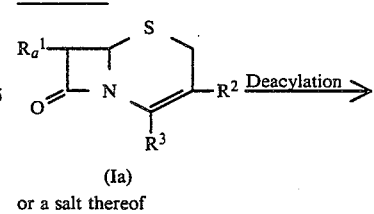

(Ia)
or a salt thereof $\xrightarrow{\text{Deacylation}}$

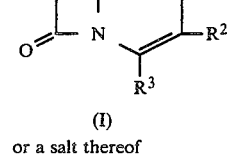

(Ib)
or a salt thereof

Process 3

(Ib)
or its reactive derivative
at the amino group
or a salt thereof $\xrightarrow{\text{Acylation}}$

(Ia)
or a salt thereof

Process 4

(Ic)
or a salt thereof $\xrightarrow{\substack{\text{Elimination of} \\ \text{carboxy protective} \\ \text{group}}}$

(Id)
or a salt thereof

Process 5

-continued (Ie) or a salt thereof
Elimination of amino protective group ⟶

(If) or a salt thereof

Process 6

(Id) or a salt thereof
Esterification ⟶

(Ib) or a salt thereof wherein
$R^1$, $R^2$ and $R^3$ are each as defined above,
$R_a^1$ is acylamino,
$R_b^1$ is acylamino having protected amino group,
$R_c^1$ is acylamino having amino group,
$R_a^3$ is protected carboxy, and
$R_b^3$ is esterified carboxy.

Among the starting compounds in the present invention, the compound (II) is novel and can be prepared by the processes which are illustrated in the following schemes.

Process A

(III) or a salt thereof
olefination ⟶

(IV) or a salt thereof

Process B

-continued (IV) or a salt thereof
oxidation ⟶

(V) or a salt thereof

Process C

(V) or a salt thereof
Dehydrohalogenation ⟶

(VI) or a salt thereof

Process D

(IVa) or a salt thereof
Deacylation ⟶

(IVb) or a salt thereof

Process E

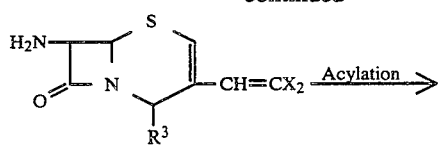

(IVb)
or its reactive derivative
at the amino group
or a salt thereof

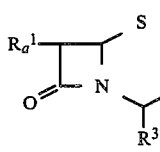

(IVa)
or a salt thereof

Process F

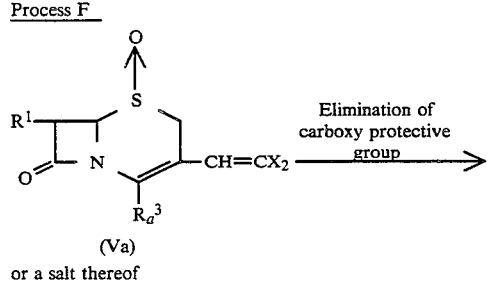

(Va)
or a salt thereof

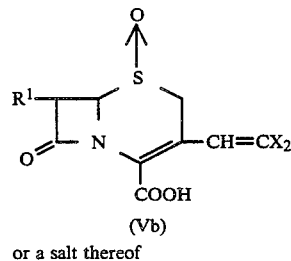

(Vb)
or a salt thereof wherein
$R^1$, $R^3$, $R_a^3$ and $R_a^1$ are each as defined above,
X is halogen, and
Ph is phenyl.

Suitable pharmaceutically acceptable salts of the object compounds (I) are conventional non-toxic salts and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, etc.), an inorganic acid salt (e.g. hydrochloride, hydrobromide, sulfate, phosphate, etc.), a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in detail as follows.

The term "lower" is intended to mean 1 to 6 carbon atom(s), unless otherwise indicated.

Suitable "acyl" and "acyl moiety" in the term "acylamino" as mentioned above may include carbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:

Aliphatic acyl such as lower or higher alkanoyl (e.g. formyl, acetyl, succinyl, hexanoyl, heptanoyl, stearoyl, etc.);
lower or higher alkoxycarbonyl (e.g. methoxycarbonyl, ethoxycarbonyl, t-butoxycarbonyl, t-pentyloxycarbonyl, heptyloxycarbonyl, etc.);
lower or higher alkanesulfonyl (e.g. methanesulfonyl, ethanesulfonyl, etc.); or the like;
Aromatic acyl such as
aroyl (e.g. benzoyl, toluoyl, naphthoyl, etc.);
ar(lower)alkanoyl such as phenyl (lower)alkanoyl (e.g. phenylacetyl, phenylpropionyl, etc.);
aryloxycarbonyl (e.g. phenoxycarbonyl, naphthyloxycarbonyl, etc.);
aryloxy(lower)alkanoyl (e.g. phenoxyacetyl, phenoxypropionyl, etc.);
arylglyoxyloyl (e.g. phenylglyoxyloyl, naphthylglyoxyloyl, etc.);
arenesulfonyl (e.g. benzenesulfonyl, p-toluenesulfonyl, etc.); or the like;
Heterocyclic acyl such as
heterocycliccarbonyl (e.g. thenoyl, furoyl, nicotinoyl, etc.);
heterocyclic(lower)alkanoyl (e.g. thienylacetyl, thiazolylacetyl, thiadiazolylacetyl, tetrazolylacetyl, etc.);
heterocyclicglyoxyloyl (e.g. thiazolylglyoxyloyl, thienylglyoxyloyl, etc.); or the like; in which suitable heterocyclic moiety in the terms "heterocycliccarbonyl", "heterocyclic(lower)alkanoyl" and "heterocyclicglyoxyloyl" as mentioned above means, in more detail, saturated or unsaturated, monocyclic or polycyclic heterocyclic group containing at least one hetero-atom such as an oxygen, sulfur, nitrogen atom and the like.

And, especially preferable heterocyclic group may be heterocyclic group such as
unsaturated 3 to 8-membered more preferably 5 or 6-membered heteromonocyclic group containing 1 to 4-nitrogen atom(s), for example, pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;
saturated 3 to 8-membered (more preferably 5 or 6-membered)heteromonocyclic group containing 1 to 4 nitrogen atom(s), for example, pyrrolidinyl, imidazolidinyl, piperidino, piperazinyl, etc.;
unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.;
unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.) etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithiolyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 to 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc. and the like.

As to the heterocyclic group as mentioned above, the following points are to be noted. That is, in case that the heterocyclic group is specifically thiazolyl or thiadiazolyl group having amino or protected amino as a substituent in its molecule, said thiazolyl or thiadiazolyl group include tautomeric isomers, which are caused by the specific behavior of the thiazole or thiadiazole ring. That is, for example, said amino- or protected aminothiazolyl or thiadiazolyl group is represented by the formula:

(A)

(wherein $R^4$ is amino or protected amino and Ya is CH or N), and in case that the group of the formula (A) takes the formula:

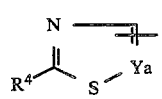
(A')

(wherein $R^4$ and Ya are each as defined above), said group of the formula (A') can be also alternatively represented by its tautomeric formula:

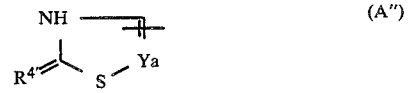
(A'')

(wherein Ya is as defined above and $R^{4'}$ is imino or protected imino). That is, both of the said groups of the formulae (A') and (A'') are in the state of tautomeric equilibrium which can be represented by the following equilibrium:

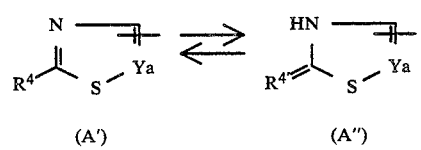

(A')          (A'')

(wherein $R^4$, Ya and $R^{4'}$ are each as defined above).

These types of tautomerism between 2-aminothiazole or thiadazole compounds and 2-iminothiazole or thiadiazoline compounds as stated above have been well known in the arts, and it is obvious to a person skilled in arts that both of the tautomeric isomers are equilibrated and lie in the reciprocably convertible state, and accordingly it is to be understood that such isomers are included within the same category or the compound per se. Accordingly, the both of the tautomeric forms are clearly included with the scope the present invention. In the present specification, the object and starting compounds including the group of such tautomeric isomers are represented by using one of the expressions therefor, i.e. 2-amino(or protected amino)thiazol or thiadiazolyl and the formula:

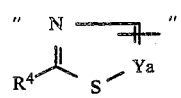

only for the convenient sake. The acyl moiety as stated above may have one to ten, same or different, suitable substituent(s) such as lower alkyl (e.g. methyl, ethyl, etc.);
lower alkoxy (e.g. methoxy, ethoxy, propoxy, etc.);
lower alkylthio (e.g. methylthio, ethylthio, etc.);
lower alkylamino (e.g. methylamino, etc.); cyclo(lower)alkyl (e.g. cyclopentyl, cyclohexyl, etc.); cyclo(lower)alkenyl (e.g. cyclohexenyl; cyclohexadienyl, etc.); halogen; amino; protected amino; hydroxy; protected hydroxy; cyano; nitro; carboxy; protected carboxy; sulfo; sulfamoyl; imino; oxo;
amino(lower)alkyl (e.g. aminomethyl, aminoethyl, etc.); carbamoyloxy;
a group of the formula $=N-OR^5$ wherein $R^5$ is hydrogen, lower alkyl (e.g. methyl, ethyl, propyl, etc.), lower alkenyl (e.g. vinyl, allyl, 2-butenyl, etc.), lower alkynyl (e.g. ethynyl, 2-propynyl, etc.), cyclo(lower)alkyl (e.g. cyclopropyl, cyclohexyl, etc.), ar(lower)alkyl such as phenyl(lower)alkyl (e.g. benzyl, phenethyl, etc.), carboxy(lower)alkyl (e.g. carboxymethyl, 1-carboxyethyl, etc.), protected carboxy(lower)alkyl or the like.

In this connection, when the acyl moiety has a group of the formula =N—OR$^5$, wherein R$^5$ is as defined above, as substituent(s), there are geometrical isomers (syn and anti isomers) due to the presence of double bond. And, for example, the syn isomer means one geometrical isomer having the group of the formula:

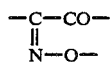

and the corresponding anti isomer means the other geometrical isomer having the group of the formula:

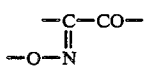

Suitable "protected amino" may include acylamino wherein "acyl" moiety can be referred to the ones as mentioned above.

Suitable protected hydroxy may include acyloxy wherein "acyl" moiety can be referred to the ones as mentioned above.

Suitable "protected carboxy" and "protected carboxy moiety" in the term "protected carboxy(lower)alkyl" may include esterified carboxy wherein "esterified carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, isobutyryloxymethyl ester, 2-ethybutyryloxymethyl ester, 3,3-dimethylbutyryloxymethyl ester, 1(or 2)-pentanoyloxyethyl ester, etc.]-lower alkanesulfonyl(lower)alkyl ester (e.g. 2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), phthalidylidene(lower)alkyl ester, or (5-lower alkyl-2-oxo-1,3-dioxol-4-yl) (lower)alkyl ester [e.g. (5-methyl-2-oxo-1,3-dioxol-4-yl) methyl ester, (5-ethyl-2-oxo-1,3-dioxol-4-yl)methyl ester, (5-propyl-2-oxo-1,3-dioxol-4-yl)ethyl ester, etc.];lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.); phthalidyl ester; and the like.

Preferable examples of the esterified carboxy as mentioned above may include lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, tert-pentyloxycarbonyl, hexyloxycarbonyl, 1-cyclopropylethoxycarbonyl, etc.), phenyl(lower)alkoxycarbonyl (e.g. benzyloxycarbonyl, benzhydryloxycarbonyl, etc.) which may have a nitro group, and lower alkanoyloxy(lower)alkoxycarbonyl (e.g., acetoxymethoxycarbonyl, pivaloyloxymethoxycarbonyl, etc.).

Suitable "halogen" and "halo" moiety in the term "dihalovinyl" may include chlorine, bromine, fluorine and iodine.

Preferred embodiments of the object compounds (I) are as follows.

Preferred embodiment of

R$^1$ is amino, lower alkanoylamino, ar(lower)alkanoylamino, more preferably phenyl(lower)alkanoylamino;

aminothiazolyl(lower)alkanoylamino having a lower alkoxyimino group, more preferably 2-lower alkoxyimino-2-aminothiazolylacetamido;

protected aminothiazolyl(lower)alkanoylamino having a lower alkoxyimino group, preferably acylaminothiazolyl(lower)alkanoylamino having a lower alkoxyimino group, more preferably 2-lower alkoxyimino-2-lower alkanoylaminothiazolylacetamido;

aminothiadiazolyl(lower)alkanoylamino having a lower alkoxyimino group, more preferably 2-lower alkoxyimino-2-aminothiadiazolylacetamido;

aminothiazolyl(lower)alkanoylamino having a carboxy(lower)alkoxyimino group, more preferably 2-carboxy(lower)alkoxyimino-2-aminothiazolylacetamido;

aminothiazolyl(lower)alkanoylamino having a protected carboxy(lower)alkoxyimino group, preferably aminothiazolyl(lower)alkanoylamino having a ar(lower) alkoxycarbonyl(lower)alkoxyimino group, more preferably 2-benzhydryloxycarbonyl(lower)alkoxyimino-2-aminothiazolylacetamido;

protected aminothiazolyl(lower)alkanoylamino having a protected carboxy(lower)alkoxyimino group, preferably acylaminothiazolyl(lower)alkanoylamino having a ar(lower) alkoxycarbonyl(lower)alkoxyimino group, more preferably 2-benzhydryloxycarbonyl(lower)alkoxyimino-2-lower alkanoylaminothiazolylacetamido;

R$^2$ is 2,2-dihalovinyl or ethynyl; and

R$^3$ is carboxy, ar(lower)alkoxycarbonyl, more preferably mono(or di)-phenyl(lower)alkoxycarbonyl or lower alkanoyloxy(lower)alkoxycarbonyl.

The processes for preparing the object compounds of the present invention are explained in detail in the following.

PROCESS 1

The compound (I) or a salt thereof can be prepared by reducing the compound (II) or a salt thereof.

The present reduction can be carried out by a conventional method which is applied for the transformation of

into —S—, for example, by using phosphorus trichloride, a combination of stannous chloride and acetyl chloride, a combination of an alkali metal iodide (e.g. sodium iodide, etc.) and trihaloacetic anhydride (e.g. trifluoroacetic anhydride, etc.), and the like.

The present reduction is usually carried out in a solvent such as acetone, dioxane, acetonitrile, dimethylformamide, benzene, hexane, chloroform, methylene chloride, ethylene chloride, tetrahydrofuran, ethyl acetate, or any other solvent which does not adversely affect the reaction.

The reaction temperature is not critical and the reaction is usually carried out under cooling or at ambient temperature.

PROCESS 2

The object compound (Ib) or a salt thereof can be prepared by subjecting the compound (Ia) or a salt thereof to deacylation reaction.

The present deacylation reaction is carried out in accordance with a conventional method such as hydrolysis; reduction; deacylation using Lewis acid; deacylation method by reacting the compound (Ia) with iminohalogenating agent and then with iminoetherifying agent, and, if necessary, subjecting the resulting compound to hydrolysis; or the like.

Among these methods, "the deacylation method by reacting the compound (Ia) with iminohalogenating agent and then with iminoetherifying agent, and, if necessary, subjecting the resulting compound to hydrolysis" is preferable method.

Suitable iminohalogenating agent may include phosphorus halide (e.g. phosphorus trichloride, phosphorus pentachloride, phosphorus tribromide, phosphorus pentabromide, etc.), phosphorus oxychloride, thionyl chloride, phosgene and the like. The reaction temperature is not critical, and the reaction is usually carried out under cooling or at ambient temperature.

In case that the compound (Ia) has a free carboxy group at the 4-position, this reaction is preferably carried out by protecting the free carboxy group with a silylating agent (e.g. trimethylsilyl chloride, trimethylsilylacetamide, bis(trimethylsilyl)acetamide, etc.) before this reaction.

Suitable iminoetherifying agent reacted with thus obtained reaction product may include an alcohol, metal alkoxide and the like. Suitable alcohol may include alkanol (e.g. methanol, ethanol, propanol, isopropanol, butanol, t-butanol, 1,3-butanediol, etc.) which may be substituted with alkoxy (e.g. methoxy, ethoxy, propoxy, isopropoxy, butoxy, etc.). Suitable metal alkoxide may include alkali metal alkoxide (e.g. sodium alkoxide, potassium alkoxide, etc.), alkaline earth metal alkoxide (e.g. calcium alkoxide, barium alkoxide, etc.) and the like. The reaction temperature is not critical, and the reaction is usually carried out under cooling or at ambient temperature.

Thus obtained product is, if necessary, subjected to hydrolysis. The hydrolysis can readily be carried out by pouring the reaction mixture obtained above into water, but there may be previously added a hydrophilic solvent (e.g. methanol, ethanol, etc.), a base (e.g. alkali metal bicarbonate, trialkylamine etc.) or an acid (e.g. diluted hydrochloric acid, acetic acid, etc.) to the water.

The reaction temperature is not critical and may be suitably selected in accordance with the kind of the protective group of the amino group and the elimination method as mentioned above, and the present reaction is preferably carried out under a mild condition such as under cooling, at ambient temperature or slightly elevated temperature.

The present invention includes, within its scope, the case that the protected carboxy is transformed into the free carboxy group according to reaction conditions and kinds of the protective groups in the course of the reaction or in posttreatment. The hydrolysis may include a method using an acid or a base and the like. These methods may be selected depending on the kind of the acyl groups to be eliminated.

Suitable acid may include an organic or an inorganic acid, for example, formic acid, trifluoroacetic acid, benzenesulfonic acid, p-toluenesulfonic acid, hydrochloric acid and the like. The acid suitable for the reaction can be selected according to the kind of acyl group to be eliminated. When the deacylation reaction is conducted with the acid, it can be carried out in the presence or absence of a solvent. Suitable solvent may include an organic solvent, water or a mixed solvent thereof. When trifluoroacetic acid is used, the deacylation reaction may be preferably carried out in the presence of anisole.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-ene, 1,4-diazabicyclo[2,2,2]octane, 1,5-diazabicyclo[5,4,0]undecene-5 or the like. The hydrolysis using a base is often carried out in water or a hydrophilic organic solvent or a mixed solvent thereof.

The reduction may include, for example, reduction with an alkali metal borohydride (e.g. sodium borohydride, etc.), catalytic reduction and the like.

The reaction temperature is not critical, and the reaction is usually carried out under cooling to warming.

PROCESS 3

The object compound (Ia) or a salt thereof can be prepared by subjecting the compound (Ib) or its reactive derivative at the amino group or a salt thereof to acylation reaction.

Suitable reactive derivative at the amino group of the compound (Ib) may include Schiff's base type imino or its tautomeric enamine type isomer formed by the reaction of the compound (Ib) with a carbonyl compound such as aldehyde, ketone or the like; a silyl derivative formed by the reaction of the compound (Ib) with a silyl compound such as bis(trimethylsilyl)acetamide, mono(trimethylsilyl)acetamide or the like; a derivative formed by reaction of the compound (Ib) with phosphorus trichloride or phosgene, and the like.

Suitable acylating agent to be used in the present acylation reaction may include conventional one and can be shown by the formula: $R^6$—OH (VIII) (wherein $R^6$ is acyl) or its reactive derivative or a salt thereof.

Suitable salt of the compounds (Ib) and (VIII) may include an acid addition salt such as an organic acid salt (e.g. acetate, maleate, tartrate, methanesulfonate, benzenesulfonate, toluenesulfonate, etc.) or an inorganic acid salt (e.g. hydrochloride, hydrobromide, sulfate, phosphate, etc.); a metal salt (e.g. sodium salt, potassium salt, calcium salt, magnesium salt, etc.); ammonium salt; an organic amine salt (e.g. triethylamine salt, dicyclohexylamine salt, etc.), and the like.

Suitable reactive derivative of the compound (VIII) may include an acid halide, an acid anhydride, an activated amide, an activated ester, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid etc.), dialkylphosphorous acid, sulforous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl [$(CH_3)_2N^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (VIII) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

When the compound (VIII) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling or at ambient temperature.

In the present reaction, a syn isomer of the object compound (Ia) can be obtained preferably by conducting the present reaction of the compound (Ib) with the corresponding syn isomer of the starting compound (VIII).

PROCESS 4

The object compound (Id) or a salt thereof can be prepared by subjecting the compound (Ic) or a salt thereof to elimination reaction of the carboxy protective group.

Suitable salt of the compound (Ic) can be referred to the salt exemplified for the compound (I).

In the present elimination reaction, all conventional methods used in the elimination reaction of the carboxy protective group, for example, hydrolysis, reduction, elimination using Lewis acid, etc. are applicable. When the carboxy protective group is an ester, it can be eliminated by hydrolysis or elimination using Lewis acid. The hydrolysis is preferably carried out in the presence of a base or an acid. Suitable base may include an inorganic base and an organic base as aforementioned.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and it may suitably be selected in accordance with the kind of the carboxy protective group and the elimination method.

The elimination using Lewis acid is preferable to eliminate substituted or unsabstituted ar(lower)alkyl ester and carried out by reacting the compound (Ic) or a salt thereof with Lewis acid such as boron trihalide (e.g. boron trichloride, boron trifluoride, etc.), titanium tetrahalide (e.g. titanium tetrachloride, titanium tetrabromide, etc.), tin tetrahalide (e.g. tin tetrachloride, tin tetrabromide etc.), aluminum halide (e.g. aluminum chloride, aluminum bromide, etc.), trihaloacetic acid (e.g. trichloroacetic acid, trifluoroacetic acid, etc.) or the like. This elimination reaction is preferably carried out in the presence of cation trapping agents (e.g. anisole, phenol, etc.) and is usually carried out in a solvent such as nitroalkane (e.g. nitromethane, nitroethane, etc.), alkylene halide (e.g. methylene chloride, ethylene chloride, etc.), diethyl ether, carbon disulfide or any other solvent which does not adversely affect the reaction. These solvents may be used as a mixture thereof.

The reductive elimination can be applied preferably for elimination of the protective group such as halo(lower)alkyl (e.g. 2-iodoethyl, 2,2,2-trichloroethyl, etc.) ester, ar(lower)alkyl (e.g. benzyl, etc.) ester or the like.

The reduction method applicable for the elimination reaction may include, for example, reduction by using a combination of a metal (e.g. zinc, zinc amalgam, etc.) or a salt of chromium compound (e.g. chromous chloride, chromous acetate, etc) and an organic or an inorganic acid (e.g. acetic acid, propionic acid, hydrochloric acid, etc.); and conventional catalytic reduction in the presence of a conventional metallic catalyst (e.g. palladium carbon, Raney nickel, etc.).

The reaction temperature is not critical, and the reaction is usually carried out under cooling, at ambient temperature or under warming.

The present elimination reaction of the carboxy protective group includes, within its scope, the cases that another protected carboxy and/or protected amino group(s) are converted into the corresponding free carboxy and/or amino group(s) during the reaction or the post-treating step of the present process.

PROCESS 5

The object compound (If) or a salt thereof can be prepared by subjecting the compound (Ie) or a salt thereof to elimination reaction of amino protective group.

Suitable salt of the compound (Ie) can be referred to the salt, exemplified for the compound (I).

The elimination reaction is carried out in accordance with a conventional method such as hydrolysis; reduction; a method treating the compound (Ie) wherein protected amino moiety is acylamino with iminohalogenating agent, iminoetherifying agent and then, if necessary, hydrolyzing the resultant; or the like. The hydrolysis may include a method using an acid or base or hydrazine and the like. These methods may be selected depending on the kind of the protective groups to be eliminated.

Among these methods, hydrolysis using an acid is one of the most common and preferable method for eliminating the protective groups such as substituted or unsubstituted alkoxycarbonyl, for example, tert-pentyloxycarbonyl, lower alkanoyl (e.g. formyl, acetyl, etc.), cycloalkoxycarbonyl, substituted or unsubstituted aralkoxycarbonyl, aralkyl (e.g. trityl), substituted phenylthio, substituted aralkylidene, substituted alkylidene, substituted cycloalkylidene or the like. Suitable acid includes an organic or inorganic acid such as formic acid, trifluoroacetic acid, benzenesulfonic acid, p-toluenesulfonic acid, hydrochloric acid and the like, and the most suitable acid is an acid which can easily be removed from the reaction mixture by a conventional manner such as distillation under reduced pressure, for example, formic acid, trifluoroacetic acid, hydrochloric acid, etc. The acids can be selected according to the kind of the protective group to be eliminated. When the elimination reaction is conducted with an acid, it can be carried out in the presence or absence of a solvent. Suitable solvent includes water, a conventional organic solvent or a mixture thereof.

The elimination reaction using trifluoroacetic acid may be carried out in the presence of anisole. The hydrolysis using hydrazine is commonly applied for eliminating a phthaloyl, succinyl type aminoprotective group.

The elimination using base is used for eliminating an acyl group such as trifluoroacetyl. Suitable base may include an inorganic base and an organic base.

The reductive elimination is generally applied for eliminating the protective group, for example, haloalkoxycarbonyl (e.g. trichloroethoxycarbonyl, etc.), substituted or unsubstituted aralkoxycarbonyl (e.g. benzyloxycarbonyl, etc.), 2-pyridylmethoxycarbonyl, etc. Suitable reduction may include, for example, reduction with an alkali metal borohydride (e.g. sodium borohydride, etc.), reduction with a combination of a metal (e.g. tin, zinc, iron, etc.) or the said metal together with a metal salt compound (e.g. chromous chloride, chromous acetate, etc.) and an organic or inorganic acid (e.g. acetic acid, propionic acid, hydrochloric acid, etc.); and catalytic reduction. Suitable catalyst includes a conventional one, for example, Raney nickel, platinum oxide, palladium carbon and the like.

Among the protective groups, the acyl group can generally be eliminated by hydrolysis. Especially, halogen substituted-alkoxycarbonyl and 8-quinolyloxycarbonyl groups are usually eliminated by treating with a heavy metal such as copper, zinc, or the like.

Among the protective groups, the acyl group can also be eliminated by treating with an iminohalogenating agent (e.g. phosphorus oxychloride, etc.) and an iminoetherifying agent such as lower alkanol (e.g. methanol, ethanol, etc.), if necessary, followed by hydrolysis.

The reaction temperature is not critical and may suitably be selected in accordance with the kind of the amino protective group and the elimination method as mentioned above, and the reaction is preferably carried out under a mild condition such as under cooling or at slightly elevated temperature.

The present invention includes, within its scope, the cases that another protected amino and/or protected carboxy group(s) are converted into the corresponding free amino and/or the free carboxy group(s) during the reaction or the post-treating step of the present process.

PROCESS 6

The object compound (Ig) or a salt thereof can be prepared by subjecting the compound (Id) or a salt thereof to esterification.

Suitable salt of the compound (Id) can be referred to the ones as exemplified for the compound (I).

The present reaction may be carried out by reacting the compound (Id) or a salt thereof with esterifying agent.

Suitable esterifying agent may be a compound of the formula: $Z-R^7$
wherein
$R^7$ is ester moiety of esterified carboxy, and
Z is hydroxy or its reactive derivative.

Suitable reactive derivative of hydroxy for Z may include an acid residue such as aforesaid halogen or the like.

The present reaction is usually carried out in a solvent such as dimethylformamide, pyridine, hexamethylphosphoric triamide, dimethylsulfoxide or any other solvent which does not adversely affect the reaction.

In case that the compound (Id) is used in a form of free acid, the reaction is preferably carried out in the presence of a base as mentioned above.

The reaction temperature is not critical and the reaction is preferably carried out under cooling, at ambient temperature or under warming.

The present esterification reaction includes, within its scope, the case that another free carboxy group in the compound (Id) is transformed into esterified carboxy group according to reaction conditions and kinds of the protective groups in the course of the reaction and/or in posttreatment of the reaction.

The present invention includes, within its scope, the cases that the one type of tautomeric isomers is converted into the other type of isomer during the reaction and/or the post-treating step of the each process.

In case that the object compound (I) is obtained in a form of the free acid at the 4-position and/or the oxime portion and/or in case that the compound (I) has free amino group, it may be transformed into its pharmaceutically acceptable salt as aforementioned by a conventional method.

The processes for preparing the starting compounds of the present invention are explained in detail in the following.

PROCESS A (III)→(IV)

The compound (IV) or a salt thereof can be prepared by subjecting the compound (III) or a salt thereof to olefination reaction.

The present reaction can be carried out by a conventional method, for example by using an olefinating agent.

Suitable olefinating agent to be used in the present olefination reaction may include the mixture of conventional one such as triphenylphosphine or hexamethylphosphorous triamide and one which can be shown by the formula:

$CX_4$ (IX) (wherein X is halogen) or $CX_2X_2^a$ (X) (wherein X is as defined above and $X^a$ is halogen the electronegativity of which is weaker than X).

The present reaction is usually carried out in a solvent such as water, acetone, dioxane, acetonitrile, chloroform, methylene chloride, tetrahydrofuran, dimethylformamide, ethyl acetate or any other solvent which does not adversely affect the reaction.

The reaction is preferably carried out in the presence of a base such as alkali metal hydroxide, alkali metal carbonate, alkali metal bicarbonate, trialkylamine, pyridine, or the like and preferably carried out around alkaline or neutral conditions. The reaction temperature is not critical and the reaction is usually carried out under cooling, at ambient temperature or under warming.

PROCESS B (IV)→(V)

The compound (V) or a salt thereof can be prepared by oxidizing the compound (IV) or a salt thereof.

The present oxidation reaction can be carried out by a conventional method which is applied for the transformation of —S— into

for example by using an oxidizing agent such as m-chloroperbenzoic acid, perbenzoic acid, peracetic acid, ozone, hydrogen peroxide, periodic acid or the like.

The present reaction is usually carried out in a solvent such as water, acetone, dioxane, acetonitrile, chloroform, methylene chloride, tetrahydrofuran, ethyl acetate or any other solvent which does not adversely affect the reaction.

The reaction temperature is not critical and the reaction is preferably carried out under cooling or at ambient temperature.

PROCESS C (V)→(VI)

The (VI) or a salt thereof can be prepared by subjecting the compound (V) or a salt thereof to dehydrohalogenation reaction.

The present dehydrohalogenation reaction is carried out in accordance with a conventional method such as dehydrohalogenation method by reacting the compound (V) with dehydrohalogenating agent, and, if necessary, subjecting the resulting compound to hydrolysis.

Suitable dehydrohalogenating agent may include alkyl lithium (e.g., n-butyl lithium), lithium diisopropylamide and the like. The reaction temperature is not critical, and the reaction is usually carried out under cooling.

Thus obtained product is, if necessary, subjected to hydrolysis. The present hydrolysis reaction can be carried out in a similar manner to that of aforementioned hydrolysis reaction in Process 2.

PROCESS D (IVa)→(IVb)

The compound (IVb) or a salt thereof can be prepared by subjecting the compound (IVa) or a salt thereof to deacylation reaction. The present reaction can be carried out in a similar manner to that of aforementioned Process 2.

PROCESS E (IVb)→(IVa)

The compound (IVa) or a salt thereof can be prepared by subjecting the compound (IVb) or its reactive derivative at the amino group or a salt thereof to acylation reaction.

The present reaction can be carried out in a similar manner to that of aforementioned Process 3.

PROCESS F (Va)→(Vb)

The compound (Vb) or a salt thereof can be prepared by subjecting the compound (Va) or a salt thereof to elimination reaction of carboxy protective group.

The present reaction can be carried out in a similar manner to that of aforementioned Process 4.

The object compounds (I) and pharmaceutically acceptable salts thereof of the present invention are novel compounds which exhibit high antibacterial activity and inhibit the growth of a wide variety of pathogenic microorganisms including Gram-positive and Gram-negative bacteria and are useful as antimicrobial agents. For therapeutic purpose, the compounds according to the present invention can be used in the form of conventional pharmaceutical preparation which contain said compounds, as an active ingredient, in admixture with a pharmaceutically acceptable carrier such as an organic or an inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives, such as lactose, fumaric acid, citric acid, tartaric acid, stearic acid, maleic acid, succinic acid, malic acid, magnesium stearate, terra alba, sucrose, corn starch, talc, gelatin, agar, pectin, peanut oil, olive oil, cacao butter, ethylene glycol and the like.

While the dosage of the compounds will vary depending upon the age and condition of the patient, an average single dose of about 10 mg., 50 mg., 100 mg., 250 mg., 500 mg., and 1000 mg. of the compounds according to the present invention was proved to be effective for treating infectious diseases caused by pathogenic bacteria. In general, amounts between 1 mg/body and about 6,000 mg/body or even more may be administered per day.

In order to illustrate the usefulness of the object compound, anti-microbial activities of a representative compound of the present invention are shown below.

[1] Test Compounds

7-[2-Carboxymethoxyimino-2-(2-aminothiazol-4-yl)-acetamido]-3-ethynyl-3-cephem-4-carboxylic acid (syn isomer). (hereinafter referred to as compound Ⓐ )

7-[2-Methoxyimino-2-(2-aminothiazol-4-yl)acetamido]-3-(2,2-dichlorovinyl)-3-cephem-4-carboxylic acid (syn isomer). (hereinafter referred to as compound Ⓑ )

[2] Test (A) Minimal inhibitory concentration

① Test Method

In vitro antibacterial activity was determined by the two-fold agar-plate dilution method as described below.

One loopful of an overnight culture of each test strain in Trypticase-soy broth ($10^8$ viable cells per ml) was streaked on heart infusion agar (HI-agar) containing graded concentrations of representative test compound, and the minimal inhibitory concentration (MIC) was expressed in terms of μg/ml after incubation at 37° C. for 20 hours.

② Test Results

| | MIC (μg/ml) | |
| | Compound | |
| Test strains | Compound Ⓐ | Compound Ⓑ |
| --- | --- | --- |
| Klebsiella pneumoniae 20 | 0.10 | 0.025 |
| Proteus mirabilis 18 | 0.05 | 0.05 |
| Proteus vulgaris 2 | 0.025 | 0.025 |

(B) Urinary excretion

① Test Method

Urine of rats was collected with a urine collector at 0 to 6, and 6 to 24 hours after oral administration of 100 mg/kg of the test antibiotic. The antibiotic levels in the urine samples were bioassayed with the standard solution prepared with M/15 phosphate buffer pH 7.0) and the urinary recovery in 24 hours was calculated.

② Test Result

| | Urinary recovery in 24 hours (%) |
| --- | --- |
| Compound Ⓐ | 20.0 |

(C) Biliary excretion

① Test Method

Rats anesthetized with pentobarbital were fixed in supine position, and a polyethylene cannula was inserted into the bile duct. Bile samples were collected at 0 to 3, 3 to 6, and 6 to 24 hours after oral administration of 100 mg/kg of the test antibiotic. The antibiotic levels in the bile samples were bioassayed with the standard solution prepared with M/15 phosphate buffer (pH 7.0) and the biliary recovery in 24 hours were calculated.

② Test Result

| | Biliary recovery in 24 hours (%) |
|---|---|
| Compound Ⓐ | 7.46 |

The following Preparations and Examples are given for the purpose of illustrating the present invention.

PREPARATION 1

Zinc powder (78.4 g) was added to a solution of benzhydryl 7-phenylacetamido-3-formyl-2-cephem-4-carboxylate (102.4 g) and triphenylphosphine (367.2 g) in a mixture of carbon tetrachloride (800 ml) and N,N-dimethylacetamide (200 ml) at ambient temperature and the mixture was stirred at 60° C. for 30 minutes. After being cooled, the mixture was added to ethyl acetate (20 l) and the resulting precipitates were filtered off and the filtrate was evaporated in vacuo. The residue was purified by column chromatography on silica gel to give benzhydryl 7-phenylacetamido-3-(2,2-dichlorovinyl)-2-cephem-4-carboxylate (15.26 g).

IR (Nujol): 1765, 1720, 1640 cm$^{-1}$.

NMR (DMSO-$d_6$, $\delta$): 3.56 (2H, s), 5.08 (1H, d, J=5 Hz), 5.45 (1H, dd, J=8 Hz, 5 Hz), 5.60 (1H, s), 6.78 (1H, s), 6.83 (1H, s), 7.05 (1H, s), 7.00–7.83 (15H, m), 9.15 (1H, d, J=8 Hz).

PREPARATION 2

The following compounds were obtained according to a similar manner to that of Preparation 1.

(1) Benzhydryl 7-phenylacetamido-3-(2,2-dibromovinyl)-2-cephem-4-carboxylate.

IR (Nujol): 3200, 1790, 1730, 1650, 1520 cm$^{-1}$.

NMR (DMSO-$d_6$, $\delta$): 3.55 (2H, s), 5.13 (1H, d, J=5 Hz), 5.45 (1H, dd, J=5,8 Hz), 5.65 (1H, s), 6.90 (1H, s), 7.1 (1H, s), 7.2–7.7 (16H, m), 9.2 (1H, d, J=8 Hz).

(2) Benzhydryl 7-phenylacetamido-3-(2,2-difluorovinyl)-2-cephem-4-carboxylate.

IR (Nujol): 3260, 1775, 1725, 1645 cm$^{-1}$.

NMR (DMSO-$d_6$, $\delta$): 3.56 (2H, s), 5.05 (1H, d, J=5 Hz), 5.25 (1H, dd, J=12 Hz, 4 Hz), 6.83 (1H, s), 7.10–7.5 (15H, m), 9.12 (1H, d, J=8 Hz).

Analysis Calcd: C: 69.92, H: 4.42, N: 5.13, S: 5.87, F: 6.95.

Found: C: 65.90, H: 4.58, N: 5.11, S: 6.00, F: 6.88.

PREPARATION 3

A solution of m-chloroperbenzoic acid (7 g) in ethyl acetate (35 ml) was added to a solution of benzhydryl 7-phenylacetamido-3-(2,2-dichlorovinyl)-2-cephem-4-carboxylate (15 g) in ethyl acetate (75 ml) under ice-cooling and the mixture was stirred at the same temperature for an hour. The precipitates were collected by filtration to give benzhydryl 7-phenylacetamido-3-(2,2-dichlorovinyl)-3-cephem-4-carboxylate-1-oxide (6.57 g).

IR (Nujol): 1780, 1725, 1645 cm$^{-1}$.

NMR (DMSO-$d_6$, $\delta$): 3.42–4.27 (2H, m), 3.62 (2H, s), 4.98 (1H, d, J=5 Hz), 5.92 (1H, dd, J=8 Hz, 5 Hz), 6.88 (1H, s), 6.95 (1H, s), 7.11–7.73 (15H, m), 8.42 (1H, d, J=8 Hz).

PREPARATION 4

The following compounds were obtained according to a similar manner to that of Preparation 3.

(1) Benzhydryl 7-[2-benzhydryloxycarbonylmethoxyimino-2-(2-formamidothiazol-4-yl) acetamido]-3-(2,2-dibromovinyl)-3-cephem-4-carboxylate-1-oxide (syn isomer).

IR (Nujol): 1790, 1710, 1680, 1650 cm$^{-1}$.

NMR (DMSO-$d_6$, $\delta$): 3.67–4.07 (2H, m), 4.93 (2H, s), 5.12 (1H, d, J=5 Hz), 6.08 (1H, dd, J=8 Hz, 5 Hz), 6.90 (1H, s), 6.95 (1H, s), 7.10–7.80 (21H, m), 8.52 (1H, s), 9.10 (1H, d, J=8 Hz).

(2) Benzhydryl 7-[2-methoxyimino-2-(2-formamidothiazol-4-yl)acetamido]-3-(2,2-dibromovinyl)-3-cephem-4-carboxylate-1-oxide (syn isomer)

IR (Nujol): 1780, 1705, 1675, 1645 cm$^{-1}$.

NMR (DMSO-$d_6$, $\delta$): 3.77–4.17 (2H, m), 3.95 (3H, s), 5.13 (1H, d, J=5 Hz), 6.07 (1H, dd, J=8 Hz, 5 Hz), 6.98 (1H, s), 7.20–7.80 (11H, m), 8.53 (1H, s), 9.18 (1H, d, J=8 Hz).

(3) Benzhydryl 7-phenylacetamido-3-(2,2-dibromovinyl)-3-cephem-4-carboxylate-1-oxide.

IR (Nujol): 1770, 1720, 1680 cm$^{-1}$.

NMR (DMSO-$d_6$, $\delta$): 3.65 (2H, s), 4.4 (2H, broad s), 5.45 (1H, d, J=5 Hz), 6.15 (1H, dd, J=5, 8 Hz), 6.98 (1H, s), 7.1–7.7 (16H, m), 8.90 (1H, d, J=8 Hz).

(4) Benzhydryl 7-formamido-3-(2,2-dibromovinyl)-3-cephem-4-carboxylate-1-oxide.

IR (Nujol): 3270, 1790, 1710, 1655 cm$^{-1}$.

NMR (DMSO-$d_6$, $\delta$): 3.67–4.17 (2H, m), 5.05 (1H, d, J=5 Hz), 6.12 (1H, dd, J=8 Hz, 5 Hz), 6.98 (1H, s), 7.2–7.77 (10H, m), 8.20 (1H, s), 8.47 (1H, d, J=8 Hz).

(5) Benzhydryl 7-phenylacetamido-3-(2,2-dibromovinyl)-3-cephem-4-carboxylate-1-oxide.

IR (Nujol): 3280, 1770, 1715, 1640 cm$^{-1}$.

NMR (DMSO-$d_6$, $\delta$): 3.67 (2H, s), 3.7–4.17 (2H, m), 4.97 (1H, d, J=4 Hz), 5.80 (1H, dd, J=12 Hz, 4 Hz), 5.07 (1H, dd, J=9 Hz, 4 Hz), 6.95 (1H, s), 7.08–7.75 (15H, m), 8.42 (1H, d, J=9 Hz).

(6) Benzhydryl 7-[2-benzhydryloxycarbonylmethoxyimino-2-(2-formamidothiazol-4-yl)acetamido]-3-(2,2-dibromovinyl)-3-cephem-4-carboxylate-1-oxide (syn isomer).

IR (Nujol): 1790, 1710, 1690 cm$^{-1}$.

NMR (DMSO-$d_6$, $\delta$): 3.3–3.6 (2H, m), 4.93 (2H, s), 5.17 (1H, d, J=5 Hz), 5.3–5.60 (1H, m), 6.13 (1H, d, J=8 Hz, 5 Hz), 6.92 (2H, s), 7.12–7.7 (21H, m), 8.53 (1H, s), 9.08 (1H, d, J=8 Hz).

PREPARATION 5

To a solution of benzhydryl 7-[2-methoxyimino-2-(2-formamidothiazol-4-yl)acetamido-3-(2,2-dibromovinyl)-3-cephem-4-carboxylate-1-oxide (syn isomer) (0.5 g) was added n-butyl lithium (1.96 ml of 1.65 M solution in hexane) at −65° to −60° C. under a nitrogen atmosphere. After the resultant mixture was stirred at the same temperature for 30 minutes, ethyl acetate (30 ml) was added to the reaction mixture. The reaction mixture was warmed to −20° C. and hydrolysed with 10% hydrochloric acid. The organic layer was separated and washed with water and brine, dried over magnesium sulfate. The solution was evaporated in vacuo to give benzhydryl 7-[2-methoxyimino-2-(2-formamidothiazol-4-yl)acetamido]-3-ethynyl-3-cephem-4-carboxylate-1-oxide (syn isomer) (0.31 g).

IR (Nujol): 1780, 1710, 1680, 1645 cm$^{-1}$.

NMR (DMSO-d$_6$, δ): 3.78–4.10 (2H, m), 3.93 (3H, s), 4.73 (1H, s), 5.08 (1H, d, J=5 Hz), 6.05 (1H, dd, J=8 Hz, 5 Hz), 7.00 (1H, s), 7.20–7.83 (11H, m), 8.53 (1H, s), 9.28 (1H, d, J=8 Hz).

PREPARATION 6

The following compounds were obtained according to a similar manner to that of Preparation 5.

(1) Benzhydryl 7-formamido-3-ethynyl-3-cephem-4-carboxylate-1-oxide

IR (Nujol): 1790, 1720, 1660 cm$^{-1}$.

Nujol (DMSO-d$_6$, δ): 3.67–4.08 (2H, m), 4.72 (1H, s), 5.02 (1H, d, J=5 Hz), 6.03 (1H, dd J=8 Hz, 5 Hz), 6.97 (1H, s), 7.12–7.78 (10H, m), 8.15 (1H, s), 8.48 (1H, d, J=8 Hz).

(2) Benzhydryl 7-[2-benzhydryloxycarbonylmethoxyimino-2-(2-formamidothiazol-4-yl)acetamido]-3-ethynyl-3-cephem-4-carboxylate-1-oxide (syn isomer)

IR (Nujol): 1790, 1710, 1680 cm$^{-1}$.

NMR (DMSO-d$_6$, δ): 3.67–4.10 (2H, m), 4.70 (1H, s), 4 90 (2H, s), 5.08 (1H, d, J=5 Hz), 6.08 (1H, dd, J=8 Hz, 5 Hz), 6.87 (1H, s), 6.97 (1H, s), 7.10–7.90 (21H, m), 8.50 (1H, s), 9.17 (1H, d, J=8 Hz).

(3) Benzhydryl 7-phenylacetamido-3-ethynyl-3-cephem-4-carboxylate-1-oxide.

IR (Nujol): 3300, 1780, 1720, 1650, 1520 cm$^{-1}$.

NMR (DMSO-d$_6$, δ): 3.62 (2H, s), 3.91 (2H, q, J=18 Hz), 4.70 (1H, s), 4.95 (1H, d, J=4 Hz), 5.85 (1H, dd, J=4, 8 Hz), 6.98 (1H, s), 7.2–7.7 (16H, m), 8.5 (1H, d, J=8 Hz).

PREPARATION 7

To a suspension of phosphorus pentachloride (13.74 g) in dichloromethane (150 ml) was dropwise added pyridine (5.34 ml) at −15° to −10° C. under stirring which was continued at the same temperature for 30 minutes. To the above mixture was added benzhydryl 7-phenylacetoamido-3-(2,2-dibromovinyl)-2-cephem-4-carboxylate (29.4 g) at −5° C. After the reaction mixture was stirred at −5° for 1.5 hours, methanol (26.62 ml) was dropwise added to the reaction mixture under cooling at −20° and the mixture was stirred at −20° C. to −5° C. for 1.5 hours. Then water (30 ml) was added to the reaction mixture under ice-cooling. After the reaction mixture was stirred for an hour at the same temperature, diisopropylether (100 ml) was added to the reaction mixture at 0° C. The resultant precipitates were collected by filtration and washed in turn with water and diisopropyl ether to give benzhydryl 7-amino-3-(2,2-dibromovinyl)-2-cephem-4-carboxylate hydrochloride (25.23 g).

IR (Nujol): 1775, 1730, 1580 cm$^{-1}$.

NMR (DMSO-d$_6$, δ): 5.03 (1H, d, J=4 Hz), 5.20 (1H, d, J=4 Hz), 5.70 (1H, s), 6.83 (1H, s), 7.08 (1H, s), 7.13–7.63 (10H, m).

PREPARATION 8

The following compounds were obtained according to a similar manner to that of Preparation 7.

Benzhydryl 7-amino-3-(2,2-difluorovinyl)-2-cephem-4-carboxylate.

IR (Nujol): 1780, 1735, 1715 cm$^{-1}$.

NMR (DMSO-d$_6$, δ): 5.03 (1H, d, J=4 Hz), 5.20 (1H, d, J=4 Hz), 5.40 (1H, s), 5.5–5.83 (1H, m), 6.68 (1H, s), 6.87 (1H, s), 7.17–7.67 (10H, m).

PREPARATION 9

To a mixture of water (100 ml), ethyl acetate (100 ml) and tetrahydrofuran (100 ml) was added benzhydryl 7-amino-3-(2,2-dibromovinyl)-2-cephem-4-carboxylate hydrochloride (5 g), and the mixture was adjusted to pH 7.0 with saturated aqueous sodium bicarbonate. The organic layer was separated, washed with brine, dried over magnesium sulfate. The solution was evaporated in vacuo, and the residue was dissolved in dichloromethane (50 ml). On the other hand, acetic anhydride (3.2 ml) and formic acid (1.29 ml) was stirred at 40° to 45° C. for 30 minutes.

The solution was added to the dichloromethane solution obtained above under ice-cooling and the resultant mixture was stirred at the same temperature for an hour. After water and ethyl acetate were added to the reaction mixture, the organic layer was separated and washed with saturated aqueous sodium bicarbonate and brine, dried over magnesium sulfate. The solution was evaporated in vacuo to give benzhydryl 7-formamido-3-(2,2-dibromovinyl)-2-cephem-4-carboxylate (4.20 g).

IR (Nujol): 1780, 1725, 1655 cm$^{-1}$.

NMR (DMSO-d$_6$, δ): 5.20 (1H, d, J=4 Hz), 5.70 (1H, dd, J=8 Hz, 4 Hz), 7.70 (1H, s), 6.90 (1H, s), 7.12 (1H, s), 7.23–7.73 (10H, m), 8.20 (1H, s), 9.17 (1H, d, J=8 Hz).

PREPARATION 10

The following compounds were obtained according to a similar manner to that of Preparation 9.

(1) Benzhydryl 7-[2-benzhydryloxycarbonylmethoxyimino-2-(2-formamidothiazol-4-yl)acetamido]-3-(2,2-dibromovinyl)-2-cephem-4-carboxylate (syn isomer).

IR (Nujol): 1760, 1740, 1680 cm$^{-1}$.

NMR (DMSO-d$_6$, δ): 4.98 (2H, s), 5.23 (1H, d, J=4 Hz), 5.63 (1H, dd, J=8 Hz, 5 Hz), 5.67 (1H, s), 6.87 (1H, s), 6.90 (1H, s), 7.16 (1H, s), 7.10–7.67 (21H, m) 8.51 (1H, s), 9.77 (1H, d, J=8 Hz).

(2) Benzhydryl 7-[2-methoxyimino-2-(2-formamidothiazol-4-yl)acetamido]-3-(2,2-dibromovinyl)-2-cephem-4-carboxylate (syn isomer).

IR (Nujol): 1765, 1725, 1680, 1640 cm$^{-1}$.

NMR (DMSO-d$_6$, δ): 3.90 (3H, s), 5.20 (1H, d, J=4 Hz), 5.63 (1H, s), 5.65 (1H, dd, J=8 Hz, 4 Hz), 6.85 (1H, s), 7.08 (1H, s), 7.20–7.70 (11H, m), 8.50 (1H, s), 9.75 (1H, d, J=8 Hz).

(3) Benzhydryl-7-[2-benzhydryloxycarbonylmethoxyimino-2-(2-formamido-thiazol-4-yl)acetamido]-3-(2,2-difluorovinyl)-2-cephem-4-carboxylate IR (Nujol): 1770, 1715 cm$^{-1}$.

NMR (DMSO-d$_6$, δ): 4.92 (2H, s), 5.20 (1H, d, J=4 Hz), 5.35 (1H, s), 5.5–5.83 (2H, m), 6.63 (1H, s), 6.9 (2H, s), 7.05–7.67 (21H, m), 8.53 (1H, s), 9.8 (1H, d, J=8 Hz).

PREPARATION 11

Trifluoroacetic acid (0.805 g) was added to a suspension of benzhydryl 7-[2-benzhydryloxycarbonylmethoxyimino-2-(2-aminothiazol-4-yl)acetamido]-3-(2,2-difluorovinyl)-3-cephem-4-carboxylate-1-oxide (syn isomer) (0.3 g) in methylene chloride (0.6 ml) and anisole (0.382 g) under ice-cooling and the mixture was stirred at the same temperature for 30 minutes. The reaction mixture was dropwise added to diisopropylether (10 ml) and the precipitates were collected by filtration. The precipitates were added to a mixture of ethyl acetate and water and the mixture was adjusted to pH 7.0 with saturated aqueous sodium bicarbonate. The separated aqueous layer was acidified to pH 3.0 with 10% hydrochloric acid and the precipitates were collected by filtration to give 7-[2-carboxymethoxyimino-2-(2-aminothiazol-4-yl)acetamido]-3-(2,2-difluorovinyl)-3-cephem-4-carboxylic acid-1-oxide (syn isomer) (0.05 g).

IR (Nujol): 1770, 1650 cm$^{-1}$.

NMR (DMSO-d$_6$, δ): 3.5–3.98 (2H, m), 4.68 (2H, s), 5.08 (1H, d, J=5 Hz), 5.34–5.70 (1H, m), 6.05 (1H, dd, J=8 Hz, 5 Hz), 6.55 (1H, s), 7.32 (2H, broad s), 9.07 (1H, d, J=8 Hz).

EXAMPLE 1

Phosphorus trichloride (0.65 ml) was added to a solution of benzhydryl 7-phenylacetamido-3-(2,2-dibromovinyl)-3-cephem-4-carboxylate-1-oxide (25 g) in N,N-dimethylformamide (20 ml) at −20° C. and the mixture was stirred at −20°∼−10° C. for 1-2 hours.

The reaction mixture was poured into a cold mixture of water and ethyl acetate under stirring. The separated organic layer was washed with brine and evaporated. The residue was triturated with diisopropyl ether to give benzhydryl 7-phenylacetamido-3-(2,2-dibromovinyl)-3-cephem-4-carboxylate (2.03 g).

IR (Nujol): 3300, 1780, 1720, 1650, 1520 cm$^{-1}$.

NMR (DMSO-d$_6$, δ): 3.60 (2H, s), 3.70 (2H, s), 5.23 (1H, d, J=5 Hz), 5.82 (1H, dd, J=5,8 Hz), 7.00 (1H, s), 7.28–7.8 (16H, m), 9.23 (1H, d, J=8 Hz).

EXAMPLE 2

The following compounds were obtained according to a similar manner to that of Example 1.

(1) Benzhydryl 7-phenylacetamido-3-(2,2-dibromovinyl)-3-cephem-4-carboxylate.

IR (Nujol): 3320, 1740, 1720, 1640 cm$^{-1}$.

NMR (DMSO-d$_6$, δ): 3.3–3.83 (2H, m), 5.12 (1H, d, J=5 Hz), 5.72 (1H, d, J=8 Hz, 5 Hz), 6.80 (1H, s), 6.80 (1H, s), 6.83 (1H, s), 7.08–7.57 (15H, m), 9.02 (1H, d, J=8 Hz).

(2) Benzhydryl 7-formamido-3-ethynyl-3-cephem-4-carboxylate.

IR (Nujol): 1780, 1720, 1670 cm$^{-1}$.

NMR (DMSO-d$_6$, δ): 3.58–4.12 (2H, m), 4.73 (1H, s), 5.25 (1H, d, J=5 Hz), 5.92 (1H, dd, J=8 Hz, 5 Hz), 6.97 (1H, s), 7.08–7.75 (10H, m), 8.17 (1H, s), 9.13 (1H, d, J=8 Hz).

(3) Benzhydryl 7-[2-benzhydryloxycarbonylmethoxyimino-2-(2-formaminothiazol-4-yl)acetamido]-3-ethynyl-3-cephem-4-carboxylate (syn isomer).

IR (Nujol): 1780, 1720, 1680 cm$^{-1}$.

NMR (DMSO-d$_6$, δ): 3.50–3.90 (2H, m), 4.67 (1H, s), 4.88 (2H, s), 5.25 (1H, d, J=5 Hz), 5.97 (1H, dd, J=8 Hz, 5 Hz), 6.86 (1H, s), 6.93 (1H, s), 7.07–7.75 (21H, m), 8.50 (1H, s), 9.75 (1H, d, J=8 Hz).

(4) Benzhydryl 7-[2-methoxyimino-2-(2-formamidothiazol-4-yl)-acetamido]-3-ethynyl-3-cephem-4-carboxylate (syn isomer).

IR (Nujol): 1770, 1705, 1650 cm$^{-1}$.

NMR (DMSO-d$_6$, δ): 3.50–4.10 (2H, m), 3.90 (3H, s), 3.67 (1H, s), 5.27 (1H, d, J=5 Hz), 5.95 (1H, dd, J=8 Hz, 5 Hz), 6.93 (1H, s), 7.13–7.72 (11H, m), 8.50 (1H, s), 9.72 (1H, d, J=8 Hz).

(5) Benzhydryl 7-phenylacetamido-3-ethynyl-3-cephem-4-carboxylate.

IR (Nujol): 3300, 1780, 1720, 1650, 1520 cm$^{-1}$.

NMR(DMSO-d$_6$, δ): 3.60 (2H, s), 3.8 (2H, q, J=18 Hz), 4.72 (1H, s), 5.25 (1H, d, J=5 Hz), 5.80 (1H, dd, 8 Hz), 7.0 (1H, s), 7.2–7.7 (16H, m), 9.21 (1H, d, J=8 Hz).

(6) 7-Phenylacetamido-3-ethynyl-3-cephem-4-carboxylic acid.

IR (Nujol): 3300, 1770, 1720 (s), 1650, 1520 cm$^{-1}$.

(7) Benzhydryl 7-amino-3-(2,2-dichlorovinyl)-3-cephem-4-carboxylate hydrochloride.

IR (Nujol): 1780, 1720, 1580 cm$^{-1}$.

(8) Benzhydryl 7-amino-3-ethynyl-3-cephem-4-carboxylate

IR (Nujol): 1775, 1720 cm$^{-1}$.

(9) Benzhydryl 7-amino-3-(2,2-dibromovinyl)-3-cephem-4-carboxylate.

IR (Nujol): 1770, 1695, 3300 cm$^{-1}$.

(10) Trifluoroacetic acid salt of 7-amino-3-ethynyl-3-cephem-4-carboxylic acid.

IR (Nujol): 1800 cm$^{-1}$.

(11) Benzhydryl 7-[2-methoxyimino-2-(2-formamidothiazol-4-yl)acetamido]-3-(2,2-dichlorovinyl)-3-cephem-4-carboxylate (syn isomer)

IR (Nujol): 3230, 1765, 1710, 1670, 1645 cm$^{-1}$.

(12) Benzhydryl 7-[2-methoxyimino-2-(2-formamidothiazol-4-yl)acetamido]-3-(2,2-dibromovinyl)-3-cephem-4-carboxylate (syn isomer).

IR (Nujol): 3200, 1780, 1710, 1680, 1650, 1540 cm$^{-1}$.

(13) Pivaloyloxymethyl 7-[2-methoxyimino-2-(2-aminothiazol-4-yl)acetamido]-3-ethynyl-3-cephem-4-carboxylate (syn isomer)

IR (Nujol): 3250, 1780, 1750, 1675, 1615 cm$^{-1}$.

(14) Benzhydryl 7-[2-benzhydryloxycarbonylmethoxyimino-2-(2-formamidothiazol-4-yl)acetamido]-3-(2,2-dichlorovinyl)-3-cephem-4-carboxylate (syn isomer).

IR (Nujol): 1780, 1720, 1680 cm$^{-1}$.

(15) Benzhydryl 7-[2-benzhydryloxycarbonylmethoxyimino-2-(2-formamidothiazol-4-yl)acetamido]-3-

(2,2-dibromovinyl)-3-cephem-4-carboxylate (syn isomer).

IR (Nujol): 1780, 1720, 1680 cm$^{-1}$.

(16) Benzhydryl 7-[2-ethoxyimino-2-(5-amino-1,2,4-thiaziazol-3-yl)acetamido]-3-ethynyl-3-cephem-4-carboxylate (syn isomer).

IR (Nujol): 1780, 1720, 1650 cm$^{-1}$.

(17) 7-[2-Ethoxyimino-2-(5-amino-1,2,4-thiaziazol-3-yl)-acetamido]-3-ethynyl-3-cephem-4-carboxylic acid (syn isomer).

IR (Nujol): 3260, 1775, 1670 cm$^{-1}$.

(18) 7-[2-Ethoxyimino-2-(5-amino-1,2,4-thiadiazol-3-yl)-acetamido]-3-(2,2-dichlorovinyl)-3-cephem-4-carboxylic acid (syn isomer).

IR (Nujol): 3200, 1775, 1670, 1620 cm$^{-1}$.

(19) 7-[2-Ethoxyimino-2-(5-amino-1,2,4-thiaziazol-3-yl)-acetamido]-3-(2,2-dibromovinyl)-3-cephem-4-carboxylic acid (syn isomer).

IR (Nujol): 3300, 1780, 1670, 1620, 1520 cm$^{-1}$.

(20) Benzhydryl 7-[2-methoxyimino-2-(2-aminothiazol-4-yl)-acetamido]-3-ethynyl-3-cephem-4-carboxylate (syn isomer).

IR (NuJol): 3250, 1770, 1715, 1670, 1605 cm$^{-1}$.

(21) Benzhydryl 7-[2-methoxyimino-2-(2-aminothiazol-4-yl)-acetamido]-3-(2,2-dichlorovinyl)-3-cephem-4-carboxylate (syn isomer).

IR (Nujol): 3300, 1760, 1715, 1675, 1605 cm$^{-1}$.

(22) 7-[2-Methoxyimino-2-(2-aminothiazol-4-yl)-acetamido]-3-ethynyl-3-cephem-4-carboxylic acid (syn isomer).

IR (Nujol): 3250, 1760, 1640, 1620 cm$^{-1}$.

(23) 7-[2-Methoxyimino-2-(2-aminothiazol-4-yl)-acetamido]-3-(2,2-dichlorovinyl)-3-cephem-4-carboxylic acid (syn isomer).

IR (Nujol): 3200, 1760, 1655 cm$^{-1}$.

(24) 7-[2-Methoxyimino-2-(2-aminothiazol-4-yl)acetamido]-3-(2,2-dibromovinyl)-3-cephem-4-carboxylic acid (syn isomer).

IR (Nujol): 3300, 1770, 1650, 1520 cm$^{-1}$.

(25) Sodium 7[-2-methoxyimino-2-(2-aminothiazol-4-yl)-acetamido]-3-ethynyl-3-cephem-4-carboxylate (syn isomer).

IR (Nujol): 1750, 1630, 1600 cm$^{-1}$.

(26) Benzhydryl 7-[2-benzhydryloxycarbonylmethoxyimino-2-(2-aminothiazol-4-yl)acetamido]-3-ethynyl-3-cephem-4-carboxylate (syn isomer).

IR (Nujol): 1780, 1720, 1675, 1605 cm$^{-1}$.

(27) Benzhydryl 7-[2-benzhydryloxycarbonylmethoxyimino-2-(2-aminothiazol-4-yl)acetamido]-3-(2,2-dichlorovinyl)-3-cephem-4-carboxylate (syn isomer).

IR (Nujol): 1770, 1720, 1680, 1615 cm$^{-1}$.

(28) Benzhydryl 7-[2-benzhydryloxycarbonylmethoxyimino-2-(2-aminothiazol-4-yl)acetamido]-3-(2,2-dibromovinyl)-3-cephem-4-carboxylate (syn isomer).

IR (Nujol): 1780, 1720, 1680 cm$^{-1}$.

(29) 7-[2-Carboxymethoxyimino-2-(2-aminothiazol-4-yl)-acetamido]-3-ethynyl-3-cephem-4-carboxylic acid (syn isomer).

IR (Nujol): 3300, 1770, 1670 cm$^{-1}$.

(30) 7-[2-Carboxymethoxyimino-2-(2-aminothiazol-4-yl)-acetamido]-3-(2,2-dichlorovinyl)-3-cephem-4-carboxylic acid (syn isomer).

IR (Nujol): 1775, 1670, 1630 cm$^{-1}$.

(31) 7-[2-Carboxymethoxyimino-2-(2-aminothiazol-4-yl)-acetamido]-3-(2,2-dibromovinyl)-3-cephem-4-carboxylic acid (syn isomer).

IR (Nujol): 3200, 1770, 1640 cm$^{-1}$.

EXAMPLE 3

Pyridine (0.39 ml) was added to a suspension of phosphorus pentachloride (1.01 ml) in dry methylene chloride (25 ml) at 5° C., and the mixture was stirred at ambient temperature for 30 minutes. Benzhydryl 7-phenylacetamido-3-(2,2-dibromovinyl)-3-cephem-4-carboxylate (2.5 g) was added to the above mixture at −10° C. and stirred for two-hours. Then, methylcellosolve (2.3 ml) was added to the reaction mixture at −30° C. and the resulting solution was stirred for an hour. To the above solution was added 5 ml of water and the separated organic layer was washed in turn with a saturated aqueous solution of sodium bicarbonate and brine, dried. The solvent was evaporated to give benzhydryl 7-amino-3-(2,2-dibromovinyl)-3-cephem-4-carboxylate (1.7 g).

IR (Nujol): 1770, 1695, 3300 cm$^{-1}$.

NMR (DMSO-d$_6$, δ): 3.78 (2H, s), 5.28 (2H, s), 6.92 (1H, s), 7.2–7.7 (11H, m).

EXAMPLE 4

The following compounds were obtained according to a similar manner to that of Example 3.

(1) Benzhydryl 7-amino-3-(2,2-dichlorovinyl)-3-cephem-4-carboxylate hydrochloride.

IR (Nujol): 1780, 1720, 1580 cm$^{-1}$.

NMR (DMSO-d$_6$, δ): 3.82 (2H, broad s), 5.30 (2H, s), 6.93 (1H, s), 7.00 (1H, s), 7.17–7.67 (10H, m).

(2) Benzhydryl 7-amino-3-ethynyl-3-cephem-4-carboxylate.

IR (Nujol): 1775, 1720 cm$^{-1}$.

NMR (DMSO-d$_6$, δ): 3.5–3.9 (2H, m), 4.60 (1H, s), 4.88 (1H, d, J=5 Hz), 5.08 (1H, d, J=5 Hz), 6.92 (1H, s), 7.08–7.73 (10H, m).

(3) Trifluoroacetic acid salt of 7-amino-3-ethynyl-3-cephem-4-carboxylic acid.

IR (Nujol): 1800 cm$^{-1}$.

EXAMPLE 5

To a stirred suspension of Vilsmeier reagent prepared from N,N-dimethylformamide (0.56 ml) and phosphorus oxychloride (0.664 ml) in tetrahydrofuran (11 ml) in a usual manner was added 2-methoxyimino-2-(2-formamidothiazol-4-yl)acetic acid (syn isomer) (1.38 g) under ice-cooling and the mixture was stirred for 30 minutes at the same temperature. To a solution of benzhydryl 7-amino-3-(2,2-dichlorovinyl)-3-cephem-4-carboxylate hydrochloride (2.5 g) and monotrimethylsilylacetamide (3.95 g) in ethyl acetate (25 ml) was added the activated acid solution obtained above at −20° C. and mixture was stirred at −20° to −10° C. for 30 minutes. After water and ethyl acetate were added to the resultant mixture, the separated organic layer was washed in turn with saturated aqueous sodium bicarbonate and brine, dried over magnesium sulfate. The solution was evaporated in vacuo to give benzhydryl 7-[2-methoxyimino-2-(2-formamidothiazol-4-yl)acetamido]-3-(2,2-dichlorovinyl)-3-cephem-4-carboxylate (syn isomer) (2.28 g).

IR (Nujol): 3230, 1765, 1710, 1670, 1645 cm$^{-1}$.

NMR (DMSO-$d_6$/$D_2O$, δ): 3.73 (2H, broad s), 3.93 (3H, s) 5.32 (1H, d, J=5 Hz), 5.98 (1H, dd, J=8 Hz, 5 Hz), 6.90 (1H, s) 6.95 (1H, s), 7.17–7.67 (11H, m), 8.53 (1H, s), 9.73 (1H, d, J=8 Hz).

EXAMPLE 6

The following compounds were obtained according to a similar manner to that of Example 5.

(1) Benzhydryl 7-[2-benzhydryloxycarbonylmethoxyimino-2-(2-formamidothiazol-4-yl)acetamido]-3-(2,2-dibromovinyl)-3-cephem-4-carboxylate (syn isomer).

IR (Nujol): 1780, 1720, 1680 cm$^{-1}$.

NMR (DMSO-$d_6$, δ): 3.67 (2H, broad s), 4.95 (2H, s), 5.28 (1H, d, J=5 Hz), 6.00 (1H, dd, J=8 Hz, 5 Hz), 6.92 (2H, each s), 7.10–7.73 (21H, m), 8.53 (1H, s), 9.78 (1H, d, J=8 Hz).

(2) Benzhydryl 7-[2-methoxyimino-2-(2-formamidothiazol-4-yl)-acetamido]-3-(2,2-dibromovinyl)-3-cephem-4-carboxylate (syn isomer).

IR (Nujol): 3200, 1780, 1710, 1680, 1650, 1540 cm$^{-1}$.

(3) Benzhydryl 7-[2-benzhydryloxycarbonylmethoxyimino-2-(2-formaminothiazol-4-yl)acetamido]-3-(2,2-dichlorovinyl)-3-cephem-4-carboxylate (syn isomer).

IR (Nujol): 1780, 1720, 1680 cm$^{-1}$.

NMR (DMSO-$d_6$, δ): 3.53–3.93 (2H, m), 4.95 (2H, s), 5.35 (1H, d, J=5 Hz), 6.05 (1H, dd, J=8 Hz, 5 Hz), 6.93 (1H, s), 6.97 (1H, s), 7.12–7.78 (21H, m), 8.57 (1H, s), 9.82 (1H, d, J=8 Hz).

(4) Benzhydryl 7-[2-ethoxyimino-2-(5-amino-1,2,4-thiaziazol-3-yl)acetamido]-3ethynyl-3-cephem-4-carboxylate (syn isomer).

IR (Nujol): 1780, 1720, 1650 cm$^{-1}$.

NMR (DMSO-$d_6$, δ): 1.25 (3H, t, J=7 Hz), 3.33–3.95 (2H, m), 4.18 (2H, q, J=7 Hz), 4.65 (1H, s), 5.23 (1H, d, J=5 Hz), 5.97 (1H, dd, J=8 Hz, 5 Hz), 6.93 (1H, s), 7.07–7.70 (10H, m), 9.60 (1H, d, J=8 Hz).

(5) Benzhydryl 7-phenylacetamido-3-ethynyl-3-cephem-4-carboxylate.

IR (Nujol): 3300, 1780, 1720, 1650, 1520 cm.

(6) Benzhydryl 7-phenylacetamido-3-(2,2-dichlorovinyl)-3-cephem-4-carboxylate.

IR (Nujol): 3320, 1740, 1720, 1640 cm$^{-1}$.

(7) Benzhydryl 7-phenylacetamido-3-(2,2-dichlorovinyl)-3-cephem-4-carboxylate.

IR (Nujol): 3300, 1780, 1720, 1650, 1520 cm$^{-1}$.

(8) 7-Phenylacetamido-3-ethynyl-3-cephem-4-carboxylic acid.

IR (Nujol): 3300, 1770, 1720 (s), 1650, 1520 cm$^{-1}$.

(9) Benzhydryl 7-formamido-3-ethynyl-3-cephem-4-carboxylate.

IR (Nujol): 1780, 1720, 1670 cm$^{-1}$.

(10) Benzhydryl 7-[2-methoxyimino-2-(2-formamidothiazol-4-yl)acetamido]-3-ethynyl-3-cephem-4-carboxylate (syn isomer).

IR (Nujol): 1770, 1705, 1650 cm$^{-1}$.

(11) Pivaloyloxymethyl 7-[2-methoxyimino-2-(2-aminothiazol-4-yl)acetamido]-3-ethynyl-3-cephem-4-carboxylate (syn isomer).

IR (Nujol): 3250, 1780, 1750, 1675, 1615 cm$^{-1}$.

(12) Benzhydryl 7-[2-benzhydryloxycarbonylmethoxyimino-2-(2-formamidothiazol-4-yl)acetamido]-3-ethynyl-3-cephem-4-carboxylate (syn isomer).

IR (Nujol): 1780, 1720, 1680, cm$^{-1}$.

(13) 7-[2-Ethoxyimino-2-(5-amino-1,2,4-thiaziazol-3-yl)-acetamido]-3-ethynyl-3-cephem-4-carboxylic acid (syn isomer).

IR (Nujol): 3260, 1775, 1670 cm$^{-1}$.

(14) 7-[2-Ethoxyimino-2-(5-amino-1,2,4-thiadiazol-3-yl)-acetamido]-3-(2,2-dichlorovinyl]-3-cephem-4-carboxylic acid (syn isomer).

IR (Nujol): 3200, 1775, 1670, 1620 cm$^{-1}$.

(15) 7-[2 Ethoxyimino-2-(5-amino-1,2,4-thiaziazol-3-yl)-acetamido]-3-(2,2-dibromovinyl)-3-cephem-4-carboxylic acid (syn isomer).

IR (Nujol): 3300, 1780, 1670, 1620, 1520 cm$^{-1}$.

(16) Benzhydryl 7-[2-methoxyimino-2-(2-aminothiazol-4-yl)-acetamido]-3-ethynyl-3-cephem-4-carboxylate (syn isomer).

IR (Nujol): 3250, 1770, 1715, 1670, 1605 cm$^{-1}$.

(17) Benzhydryl 7-[2-methoxyimino-2-(2-aminothiazol-4-yl)-acetamido]-3-(2,2-dichlorovinyl)-3-cephem-4-carboxylate (syn isomer).

IR (Nujol): 3300, 1760, 1715, 1675, 1605 cm$^{-1}$.

(18) 7-[2-Methoxyimino-2-(2-aminothiazol-4-yl)acetamido]-3-ethynyl-3-cephem-4-carboxylic acid (syn isomer).

IR (Nujol): 3250, 1760, 1640, 1620 cm$^{-1}$.

(19) 7-[2-Methoxyimino-2-(2-aminothiazol-4-yl)acetamido]-3-(2,2-dichlorovinyl)-3-cephem-4-carboxylic acid (syn isomer).

IR (Nujol): 3200, 1760, 1655 cm$^{-1}$.

(20) 7-[2-Methoxyimino-2-(2-aminothiazol-4-yl)acetamido]-3-(2,2-dibromovinyl)-3-cephem-4-carboxylic acid (syn isomer).

IR (Nujol): 3300, 1770, 1650, 1520 cm$^{-1}$.

(21) Sodium 7-[2-methoxyimino-2-(2-aminothiazol-4-yl)-acetamido]3-ethynyl-3-cephem-4-carboxylate (syn isomer).

IR (Nujol): 1750, 1630, 1600 cm$^{-1}$.

(22) Benzhydryl 7-[2-benzhydryloxycarbonylmethoxyimino-2-(2-aminothiazol-4-yl)acetamido]-3-ethynyl-3-cephem-4-carboxylate (syn isomer).

IR (Nujol): 1780, 1720, 1675, 1605 cm$^{-1}$.

(23) Benzhydryl 7-[2-benzhydryloxycarbonylmethoxyimino-2-(2-aminothiazol-4-yl)acetamido]-3-(2,2-dichlorovinyl)-3-cephem-4-carboxylate (syn isomer).

IR (Nujol): 1770, 1720, 1680, 1615 cm$^{-1}$.

(24) Benzhydryl 7-[2-benzhydryloxycarbonylmethoxyimino-2-(2-aminothiazol-4-yl)acetamido]-3-(2,2-dibromovinyl)-3-cephem-4-carboxylate (syn isomer).

IR (Nujol): 1780, 1720, 1680 cm$^{-1}$.

(25) 7-[2-Carboxymethoxyimino-2-(2-aminothiazol-4-yl)-acetamido]-3-ethynyl-3-cephem-4-carboxylic acid (syn isomer).

IR (Nujol): 3300, 1770, 1670 cm$^{-1}$.

(26) 7-[2-Carboxymethoxyimino-2-(2-aminothiazol-4-yl)-acetamido]-3-(2,2-dichlorovinyl)-3-cephem-4-carboxylic acid (syn isomer).

IR (Nujol): 1775, 1670, 1630 cm$^{-1}$.

(27) 7-[2-Carboxymethoxyimino-2-(2-aminothiazol-4-yl)-acetamido]-3-(2,2-dibromovinyl)-3-cephem-4-carboxylic acid (syn isomer).

IR (Nujol): 3200, 1770, 1640 cm$^{-1}$.

(28) Benzhydryl 7-[2-ethoxyimino-2-(5-amino-1,2,4-thiaziazol-3-yl)acetamido]-3-(2,2-dibromovinyl)-3-cephem-4-carboxylate (syn isomer).

(29) Benzhydryl 7-[2-ethoxyimino-2-(5-amino-1,2,4-thiadiazol-3-yl)acetamido]-3-(2,2-dichlorovinyl)-3-cephem-4-carboxylate (syn isomer)

EXAMPLE 7

To a solution of benzhydryl 7-[2-methoxyimino-2-(2-formamidothiazol-4-yl)acetamido]-3-(2,2-dichlorovinyl)-3-cephem-4-carboxylate (syn isomer) (2.2 g) in methanol (11 ml) was added conc. hydrochloric acid (0.72 ml) and the resulting mixture was stirred at ambient temperature for 3 hours. To the reaction mixture were added water and ethyl acetate, the mixture was adjusted to pH 7.0 with saturated aqueous sodium bicarbonate, the separated organic layer was washed with brine, dried over magnesium sulfate. The solution was evaporated in vacuo to give benzhydryl 7-[2-methoxyimino-2-(2-aminothiazol-4-yl)-acetamido]-3-(2,2-dichlorovinyl)-3-cephem-4-carboxylate (syn isomer) (1.98 g).

IR (Nujol): 3300, 1760, 1715, 1675, 1605 cm$^{-1}$.

NMR (DMSO-d$_6$/D$_2$, δ): 3.73 (2H, broad s), 3.88 (3H, s), 5.30 (1H, d, J=5 Hz), 5.95 (1H, dd, J=8 Hz, 5 Hz), 6.77 (1H, s), 6.90 (1H, s), 6.95 (1H, s), 7.07–7.67 (10H, m), 9.63 (1H, d, J=8 Hz).

EXAMPLE 8

The following compounds were obtained according to a similar manner to that of Example 7.

(1) Benzhydryl 7-2-benzhydryloxycarbonylmethoxyimino-2-(2-aminothiazol-4-yl)acetamido]-3-ethynyl-3-cephem-4-carboxylate (syn isomer).

IR (Nujol): 1780, 1720, 1675, 1605 cm$^{-1}$.

NMR (DMSO-d$_6$, δ): 3.57–3.77 (2H, m), 4.67 (1H, s), 4.83 (2H, s), 5.25 (1H, d, J=5 Hz), 5.93 (1H, dd, J=8 Hz), 6.76 (1H, s), 6.86 (1H, s), 6.93 (1H, s), 7.00–7.77 (20H, m), 9.65 (1H, d, J=8 Hz).

(2) Benzhydryl 7-[2-methoxyiminio-2-(2-aminothiazol-4-yl)-acetamido]-3-ethynyl-3-cephem-4-carboxylate (syn isomer).

IR (Nujol): 3250, 1770, 1715, 1670, 1605 cm$^{-1}$.

NMR (DMSO-d$_6$, δ): 3.50–3.95 (2H, m), 3.83 (3H, s), 4.65 (1H, s), 5.23 (1H, d, J=5 Hz), 5.90 (1H, dd, J=8 Hz, 5 Hz), 6.73 (1H, s), 6.93 (1H, s), 7.00–7.67 (10H, m), 9.60 (1H, d, J=8 Hz).

(3) Benzhydryl 7-2-Benzhydryloxycarbonylmethoxyimino-2-(2-aminothiazol-4-yl)acetamido]-3-(2,2-dichlorovinyl)-3-cephem-4-carboxylate (syn isomer).

IR (Nujol): 1770, 1720, 1680, 1615 cm$^{-1}$.

NMR (DMSO-d$_6$, δ): 3.53 (2H, broad s), 4.83 (2H, s), 5.20 (1H, d, J=5 Hz), 5.98 (1H, dd, J=8 Hz, 5 Hz), 6.80 (1H, s), 6.90 (1H, s), 6.93 (1H, s), 7.02–7.80 (20H, m), 9.67 (1H, d, J=8 Hz).

(4) Benzhydryl 7-2-benzhydryloxycarbonylmethoxyimino-2-(2-aminothiazol-4-yl)acetamido]-3-(2,2-dibromovinyl)-3-cephem-4-carboxylate (syn isomer).

IR (Nujol): 1780, 1720, 1680 cm$^{-1}$.

NMR (DMSO-d$_6$, δ): 3.62 (2H, broad s), 4.85 (2H, s), 5.25 (1H, d, J=5 Hz), 5.95 (1H, dd, J=8 Hz, 5 Hz), 6.78 (2H, each s), 6.90 (1H, s), 6.95–7.67 (20H, m), 9.67 (1H, d, J=8 Hz).

(5) Benzhydryl 7-[2-ethoxyimino-2-(5-amino-1,2,4-thiadiazol-3-yl)-acetamido]-3-ethynyl-3-cephem-4-carboxylate (syn isomer).

IR (Nujol): 1780, 1720, 1650 cm$^{-1}$.

(6) 7-[2-Ethoxyimino-2-(5-amino-1,2,4-thiadiazol-3-yl)-acetamido]-3-ethynyl-3-cephem-4-carboxylic acid (syn isomer).

IR (Nujol): 3260, 1775, 1670 cm$^{-1}$.

(7) 7-[2-Ethoxyimino-2-(5-amino-1,2,4-thiadiazol-3-yl)-acetamido]-3-(2,2-dichlorovinyl)-3-cephem-4-carboxylic acid (syn isomer).

IR (Nujol): 3200, 1775, 1670, 1620 cm$^{-1}$.

(8) 7-[2-Ethoxyimino-2-(5-amino-1,2,4-thiaziazol-3-yl)-acetamido]-3-(2,2-dibromovinyl)-3-cephem-4-carboxylic acid (syn isomer).

IR (Nujol): 3300, 1780, 1670, 1620, 1520 cm$^{-1}$.

(9) 7-[2-Methoxyimino-2-(2-aminothiazol-4-yl)acetamido]-3-ethynyl-3-cephem-4-carboxylic acid (syn isomer).

IR (Nujol): 3250, 1760, 1640, 1620 cm$^{-1}$.

(10) 7-[2-Methoxyimino-2-(2-aminothiazol-4-yl)-acetamido]-3-(2,2-dichlorovinyl)-3-cephem-4-carboxylic acid (syn isomer).

IR (Nujol): 3200, 1760, 1655 cm$^{-1}$.

(11) 7-[2-Methoxyimino-2-(2-aminothiazol-4-yl)acetamido]-3-(2,2-dibromovinyl)-3-cephem-4-carboxylic acid (syn isomer).

IR (Nujol): 3300, 1770, 1650, 1520 cm$^{-1}$.

(12) Sodium 7-[2-methoxyimino-2-(2-aminothiazol-4-yl)-acetamido]-3-ethynyl-3-cephem-4-carboxylate (syn isomer).

IR (Nujol): 1750, 1630, 1600 cm$^{-1}$.

(13) 7-[2-Carboxymethoxyimino-2-(2-aminothiazol-4-yl)-acetamido]-3-ethynyl-3-cephem-4-carboxylic acid (syn isomer).

IR (Nujol): 3300, 1770, 1670 cm$^{-1}$.

(14) 7-[2-Carboxymethoxyimino-2-(2-aminothiazol-4-yl)-acetamido]-3-(2,2-dichlorovinyl)-3-cephem-4-carboxylic acid (syn isomer).

IR (Nujol): 1775, 1670, 1630 cm$^{-1}$.

(15) 7-[2-Carboxymethoxyimino-2-(2-aminothiazol-4-yl)-acetamido]-3-(2,2-dibromovinyl)-3-cephem-4-carboxylic acid (syn isomer).

IR (Nujol): 3200, 1770, 1640 cm$^{-1}$.

(16) Pivaloyloxymethyl 7-[2-methoxyimino-2-(2-aminothiazol-4-yl)acetamido]-3-ethynyl-3-cephem-4-carboxylate (syn isomer).

IR (Nujol): 3250, 1780, 1750, 1675, 1615 cm$^{-1}$.

EXAMPLE 9

(1) To a suspension of benzhydryl 7-[2-methoxyimino-2-(2-aminothiazol-4-yl)acetamido]-3-ethynyl-3- cephem-4-carboxylate (syn isomer) (3.70 g) and anisole (5.58 g) was added trifluoroacetic acid (14.71 g) under ice-cooling and the resultant mixture was stirred at the same temperature for 30 minutes. The reaction mixture was dropwise added to diisopropylether (200 ml) and the precipitates were collected by filtration. The precipitates were added to water and ethyl acetate and the mixture was adjusted to pH 7.0 with saturated aqueous sodium bicarbonate. The separated aqueous layer was acidified to pH 3.0 with 10% hydrochloric acid and the precipitates were collected by filtration to give 7-[2-methoxyimino-2-(2-aminothiazol-4-yl)acetamido]-3-ethynyl-3-cephem-4-carboxylic acid (syn isomer) (1.55 g).

IR (Nujol): 3250, 1760, 1640, 1620 cm$^{-1}$.

NMR (DMSO-$d_6$, $\delta$): 3.50–3.90 (2H, m), 3.80 (3H, s), 4.45 (1H, s), 5.15 (1H, d, J=5 Hz), 5.78 (1H, dd, J=8 Hz, 5 Hz), 6.67 (1H, s), 7.10 (2H, broad s), 9.55 (1H, d, J=8 Hz).

(2) To a solution of 7-[2-methoxyimino-2-(2-aminothiazol-4-yl)acetamido]-3-ethynyl-3-cephem-4-carboxylic acid (syn isomer) (1.1 g) in tetrahydrofuran (22 ml) was added a solution of sodium acetate (0.234 g) in methanol (2.3 ml) at ambient temperature. After the mixture was stirred under ice-cooling for 30 minutes, the precipitates were collected by filtration to give sodium 7-[2-methoxyimino-2-(2-aminothiazol-4-yl)acetamido]-3-ethynyl-3-cephem-4-carboxylate (syn isomer) (1.16 g).

IR (Nujol): 1750, 1630, 1600 cm$^{-1}$.

EXAMPLE 10

To a solution of benzhydryl 7-[2-methoxyimino-2-(2-formamidothiazol-4-yl)acetamido]-3-(2,2-dibromovinyl)-3-cephem-4-carboxylate (syn isomer) (1 g) in methanol (5 ml) was added conc. hydrochloric acid (0.5 ml) and the resulting mixture was stirred at ambient temperature for 2 hours. Then, the reaction mixture was poured into ice-water and adjusted to pH 3.5 with a saturated aqueous solution of sodium bicarbonate. The precipitate was collected by filtration, dried and dissolved in a mixture of trifluoroacetic acid (5 ml) and anisole (0.5 ml) at ambient temperature. After trifluoroacetic acid was evaporated in vacuo, the residue was added to a mixture of ethyl acetate and water and adjusted to pH 3.0 with a saturated aqueous solution of sodium bicarbonate. The separated organic layer was evaporated to give 7-[2-methoxyimino-2-(2-aminothiazol-4-yl)acetamido]-3-(2,2-dibromovinyl)-3-cephem-4-carboxylic acid (syn isomer) (0.35 g).

IR (Nujol): 3300, 1770, 1650, 1520 cm$^{-1}$.

NMR ($d_6$-DMSO, $\delta$): 3.65 (2H, s), 3.82 (3H, s), 5.15 (1H, d, J=4 Hz), 5.80 (1H, dd, J=4, 8 Hz), 6.70 (1H, s), 7.40 (1H, s), 9.55 (1H, d, J=8 Hz).

EXAMPLE 11

The following compounds were obtained according to similar manners to those of Examples 9 to 10.

(1) 7-[2-Ethoxyimino-2-(5-amino-1,2,4-thiaziazol-3-yl)-acetamido]-3-ethynyl-3-cephem-4-carboxylic acid (syn isomer).

IR (Nujol): 3260, 1775, 1670 cm$^{-1}$.

NMR (DMSO-$d_6$, $\delta$): 1.25 (3H, t, J=7 Hz), 3.38–3.88 (2H, m), 4.18 (2H, q, J=7 Hz), 4.45 (1H, s), 5.18 (1H, d, J=5 Hz), 5.85 (1H, dd, J=8 Hz, 5 Hz), 8 10 (2H, broad s), 9.55 (1H, d, J=8 Hz).

(2) 7-[2-Carboxymethoxyimino-2-(2-aminothiazol-4-yl)-acetamido]-3-ethynyl-3-cephem-4-carboxylic acid (syn isomer).

IR (Nujol): 3300, 1770, 1670 cm$^{-1}$.

NMR (DMSO-$d_6$, $\delta$): 3.37–4.02 (2H, m), 4.48 (1H, s), 4.58 (2H, s), 5.18 (1H, d, J=5 Hz), 5.83 (1H, dd, J=8 Hz, 5 Hz), 7.75 (1H, s), 7.20 (2H, broad s), 9.48 (1H, d, J=8 Hz).

(3) 7-Phenylacetamido-3-ethynyl-3-cephem-4-carboxylic acid.

IR (Nujol): 3300, 1770, 1720 (s), 1650, 1520 cm$^{-1}$.

NMR (DMSO-$d_6$, $\delta$): 3.52 (2H, s), 3.55 (2H, broad s), 4.50 (1H, s), 5.15 (1H, d, J=5 Hz), 5.75 (1H, dd, J=5, 8 Hz), 7.30 (5H, m), 9.15 (1H, d, J=8 Hz).

(4) Trifluoroacetic acid salt of 7-amino-3-ethynyl-3-cephem-4-carboxylic acid.

IR (Nujol): 1800 cm$^{-1}$.

NMR (DMSO-$d_6$, $\delta$): 3.23–3.95 (2H, m), 4.43 (1H, s), 4.85 (1H, d, J=5 Hz), 5.05 (1H, d, J=5 Hz), 7.3 (2H, broad s).

(5) 7-[2-Carboxymethoxyimino-2-(2-aminothiazol-4-yl)-acetamido]-3-(2,2-dibromovinyl)-3-cephem-4-carboxylic acid (syn isomer).

IR (Nujol): 3200, 1770, 1640 cm$^{-1}$.

NMR (DMSO-$d_6$, $\delta$): 3.45–3.9 (2H, m), 4.58 (2H, s), 5.17 (1H, d, J=5 Hz), 5.83 (1H, dd, J=8 Hz, 5 Hz), 6.77 (1H, s), 7.23 (2H, broad s), 7.42 (1H, s), 9.49 (1H, d, J=8 Hz).

(6) 7-[2-Carboxymethoxyimino-2-(2-aminothiazol-4-yl)-acetamido]-3-(2,2-dichlorovinyl)-3-cephem-4-carboxylic acid (syn isomer).

IR (Nujol): 1775, 1670, 1630 cm$^{-1}$.

NMR (DMSO-$d_6$, $\delta$): 3.77 (2H, broad s), 4.67 (2H, s), 5.30 (1H, d, J=5 Hz), 5.93 (1H, dd, J=8 Hz, 5 Hz), 6.87 (1H, s), 7.03 (1H, s), 9.55 (1H, d, J=8 Hz).

(7) 7-[2-Methoxyimino-2-(2-aminothiazol-4-yl)-acetamido]-3-(2,2-dichlorovinyl)-3-cephem-4-carboxylic acid (syn isomer).

IR (Nujol): 3200, 1760, 1655 cm$^{-1}$.

NMR (DMSO-$d_6$, $D_2O$, $\delta$): 3.68 (2H, broad s), 3.83 (3H, s), 5.20 (1H, d, J=5 Hz), 5.82 (1H, dd, J=8 Hz, 5 Hz), 6.75 (1H, s), 6.95 (1H, s), 9.60 (1H, d, J=8 Hz).

(8) 7-[2-Ethoxyimino-2-(5-amino-1,2,4-thiadiazol-3-yl)-acetamido]-3-(2,2-dichlorovinyl)-3-cephem-4-carboxylic acid (syn isomer).

IR (Nujol): 3200, 1775, 1670, 1620 cm$^{-1}$.

NMR (DMSO-$d_6$, $\delta$): 1.28 (3H, t, J=7 Hz), 3.72 (2H, broad s), 4.22 (2H, q, J=7 Hz), 5.23 (1H, d, J=5 Hz), 5.88 (1H, dd, J=8 Hz, 5 Hz), 7.03 (1H, s), 8.13 (2H, broad s), 9.57 (1H, d, J=8 Hz).

(9) 7-[2-Ethoxyimino-2-(5-amino-1,2,4-thiadiazol-3-yl)-acetamido]-3-(2,2-dibromovinyl)-3-cephem-4-carboxylic acid (syn isomer).

IR (Nujol): 3300, 1780, 1670, 1620, 1520 cm$^{-1}$.

NMR (DMSO-$d_6$, $\delta$): 1.26 (3H, t, J=7 Hz), 3.7 (2H, s), 4.21 (2H, q, J=7 Hz), 5.21 (1H, d, J=5 Hz), 5.91 (1H, dd, J=5, 8 Hz), 7.48 (1H, s), 8.0-8.4 (2H, broad s), 9.60 (1H, d, J=8 Hz).

EXAMPLE 12

To a solution of sodium 7-[2-methoxyimino-2-(2-aminothiazol-4-yl)acetamido]-3-ethynyl-3-cephem-4-carboxylate (syn isomer) (1.1 g) was added iodomethyl pivalate (0.744 g) under ice-cooling and the resultant mixture was stirred at the same temperature for 10 minutes. After the reaction mixture was added to a stirred mixture of water and ethyl acetate, the separated organic solution was washed in turn with water, saturated aqueous sodium bicarbonate and brine, and dried over magnesium sulfate. The solution was evaporated in vacuo to give pivaloyloxymethyl 7-[2-methoxyimino-2-(2-aminothiazol-4-yl)-acetamido]-3-ethynyl-3-cephem-4-carboxylate (syn isomer) (0.82 g).

IR (Nujol): 3250 1780, 1750, 1675, 1615 cm$^{-1}$.

NMR (DMSO-d$_6$, δ): 1.13 (9H, s), 3.50-4.18 (2H, m), 3.80 (3H, s), 4.63 (1H, s), 5.22 (1H, d, J=5 Hz), 5.84 (1H, dd, J=8 Hz), 5.85 (2H, s), 6.72 (1H, s), 7.20 (2H, broad s), 9.60 (1H, d, J=8 Hz).

EXAMPLE 13

The following compound were obtained according to a similar manner to that of Example 12.

(1) Benzhydryl 7-phenylacetamido-3-ethynyl-3-cephem-4-carboxylate.

IR (Nujol): 3300, 1780, 1720, 1650, 1520 cm$^{-1}$.

(2) Benzhydryl 7-phenylacetamido-3-(2,2-dichlorovinyl)-3-cephem-4-carboxylate.

IR (Nujol): 3320, 1740, 1720, 1640 cm$^{-1}$.

(3) Benzhydryl 7-phenylacetamido-3-(2,2-dibromovinyl)-3-cephem-4-carboxylate.

IR (Nujol): 3300, 1780, 1720, 1650, 1520 cm$^{-1}$.

(4) Benzhydryl 7-amino-3-(2,2-dichlorovinyl)-3-cephem-4-carboxylate hydrochloride.

IR (Nujol): 1780, 1720, 1580 cm$^{-1}$.

(5) Benzhydryl 7-amino-3-ethynyl-3-cephem-4-carboxylate.

IR (Nujol): 1775, 1720 cm$^{-1}$.

(6) Benzhydryl 7-amino-3-(2,2-dibromovinyl)-3-cephem-4-carboxylate.

IR (Nujol): 1770, 1695, 3300 cm$^{-1}$.

(7) Benzhydryl 7-formamido-3-ethynyl-3-cephem-4-carboxylate.

IR (Nujol): 1780, 1720, 1670 cm$^{-1}$.

(8) Benzhydryl 7-[2-methoxyimino-2-(2-formamidothiazol-4-yl)acetamido]-3-ethynyl-3-cephem-4-carboxylate (syn isomer).

IR (Nujol): 1770 1705 1650 cm$^{-1}$.

(9) Benzhydryl 7-[2-methoxyimino-2-(2-formamidothiazol-4-yl)acetamido]-3-(2,2-dichlorovinyl)-3-cephem-4-carboxylate (syn isomer).

IR (Nujol): 3230, 1765, 1710, 1670, 1645 cm$^{-1}$.

(10) Benzhydryl 7-[2-methoxyimino-2-(2-formamidothiazol-4-yl)acetamido]-3-(2,2-dibromovinyl)-3-cephem-4-carboxylate (syn isomer).

IR (Nujol): 3200, 1780, 1710, 1680, 1650, 1540 cm$^{-1}$.

(11) Benzhydryl 7-[2-benzhydryloxycarbonylmethoxyimino-2-(2-formamidothiazol-4-yl)acetamido]-3-ethynyl-3-cephem-4-carboxylate (syn isomer).

IR (Nujol): 1780, 1720, 1680 cm$^{-1}$.

(12) Benzhydryl 7-[2-benzhydryloxycarbonylmethoxyimino-2-(2-formamidothiazol-4-yl)acetamido]-3-(2,2-dichlorovinyl)-3-cephem-4-carboxylate (syn isomer).

IR (Nujol): 1780, 1720, 1680 cm$^{-1}$.

(13) Benzhydryl 7-[2-benzhydryloxycarbonylmethoxyimino-2-(2-formamidothiazol-4-yl)acetamido]-3-(2,2-dibromovinyl)-3-cephem-4-carboxylate (syn isomer).

IR (Nujol): 1780, 1720, 1680 cm$^{-1}$.

(14) Benzhydryl 7-[2-ethoxyimino-2-(5-amino-1,2,4-thiaziazol-3-yl)acetamido]-3-ethynyl-3-cephem-4-carboxylate (syn isomer).

IR (Nujol): 1780, 1720, 1650 cm$^{-1}$.

(15) Benzhydryl 7-[2-methoxyimino-2-(2-aminothiazol-4-yl)-acetamido]-3-ethynyl-3-cephem-4-carboxylate (syn isomer).

IR (Nujol): 3230, 1770, 1715, 1670, 1605 cm$^{-1}$.

(16) Benzhydryl 7-[2-methoxyimino-2-(2-aminothiazol-4-yl)-acetamido]-3-(2,2-dichlorovinyl)-3-cephem-4-carboxylate (syn isomer).

IR (Nujol): 3300, 1760, 1715, 1675, 1605 cm$^{-1}$.

(17) Benzhydryl 7-[2-benzhydryloxycarbonylmethoxyimino-2-(2-aminothiazol-4-yl)acetamido]-3-ethynyl-3-cephem-4-carboxylate (syn isomer).

IR (Nujol): 1780, 1720, 1675, 1605 cm$^{-1}$.

(18) Benzhydryl 7-[2-benzhydryloxycarbonylmethoxyimino-2-(2-aminothiazol-4-yl)acetamido]-3-(2,2-dichlorovinyl)-3-cephem-4-carboxylate (syn isomer).

IR (Nujol): 1770, 1720, 1680, 1615 cm$^{-1}$.

(19) Benzhydryl 7-[2-benzhydryloxycarbonylmethoxyimino-2-(2-aminothiazol-4-yl)acetamido]-3-(2,2-dibromovinyl)-3-cephem-4-carboxylate (syn isomer).

IR (Nujol): 1780, 1720, 1680 cm$^{-1}$.

(20) Benzhydryl 7-[2-ethoxyimino-2-(5-amino 1,2,4-thiaziazol-3-yl)acetamido]-3-(2,2-dibromovinyl)-3-cephem-4-carboxylate (syn isomer).

(21) Benzhydryl 7-[2-ethoxyimino-2-(5-amino-1,2,4-thiadiazol-3-yl)acetamido]-3-(2,2-dichlorovinyl)-3-cephem-4-carboxylate (syn isomer).

What we claim is:

1. Cephem compounds of the formula:

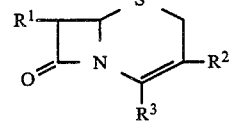

wherein $R^1$ is amino, lower alkanoylamino, ar(lower)alkanoylamino, amino- or alkanoylthiazolyl(lower)alkanoylamino having a lower alkoxyimino, amino- or alkanoylthiazolyl(lower)alkanoylamino having a ar(lower)alkoxycarbonyl(lower)alkoxyimino, aminothiazolyl(lower)alkanoylamino having a carboxy(lower)alkoxyimino, or aminothiadiazolyl(lower)alkanoylamino having a lower alkoxyimino, $R^2$ is 2,2-dihalovinyl, and $R^3$ is carboxy or protected carboxy, and pharmaceutically acceptable salts thereof.

2. A compound of claim 1, wherein
R³ is carboxy, ar(lower)alkoxycarbonyl, or lower alkanoyloxy(lower)alkoxycarbonyl.

3. A compound of claim 2, wherein
R¹ is amino, formamido, phenylacetamido, aminothiazolylacetamido having methoxyimino, formamidothiazolylacetamido having methoxyimino, aminothiazolylacetamido having benzhydryloxycarbonylmethoxyimino, formamidothiazolylacetamido having benzhydryloxycarbonylmethoxyimino, aminothiazolylacetamido having carboxymethoxyimino, or aminothiadiazolylacetamido having ethoxyimino,
R² is 2,2-dichlorovinyl or 2,2-dibromovinyl, and
R³ is carboxy, benzhydryloxycarbonyl, or pivaloyloxymethoxycarbonyl.

4. Syn isomer of a compound of claim 3, wherein
R¹ is 2-methoxyimino-2-(2-aminothiazol-4-yl)acetamido, 2-carboxymethoxyimino-2-(2-aminothiazol-4-yl)-acetamido, or 2-ethoxyimino-2-(5-amino-1,2,4-thiadiazol-3-yl)acetamido, and
R³ is carboxy.

5. A compound of claim 4, which is selected from the compound consisting of:
7-[2-methoxyimino-2-(2-aminothiazol-4-yl)-acetamido]-3-(2,2-dichlorovinyl)-3-cephem-4-carboxylic acid (syn isomer),
7-[2-carboxymethoxyimino-2-(2-aminothiazol-4-yl)acetamido]-3-(2,2-dichlorovinyl)-3-cephem-4-carboxylic acid (syn isomer),
7-[2-ethoxyimino-2-(5-amino-1,2,4-thiadiazol-3-yl)acetamido]-3-(2,2-dichlorovinyl)-3-cephem-4-carboxylic acid (syn isomer),
7-[2-methoxyimino-2-(2-aminothiazol-4-yl)-acetamido]-3-(2,2-dibromovinyl)-3-cephem-4-carboxylic acid (syn isomer),
7-[2-carboxymethoxyimino-2-(2-aminothiazol-4-yl)acetamido]-3-(2,2-dibromovinyl)-3-cephem-4-carboxylic acid (syn isomer), and
7-[2-ethoxyimino-2-(5-amino-1,2,4-thiadiazol-3-yl)acetamido]-3-(2,2-dibromovinyl)-3-cephem-4-carboxylic acid (syn isomer).

6. Cephem compounds of the formula:

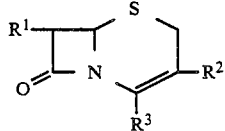

wherein
R¹ is amino, lower alkanoylamino, ar(lower)alkanoylamino, amino- or alkanoylthiazolyl(lower)alkanoylamino having a lower alkoxyimino, amino- or alkanoylthiazolyl(lower)alkanoylamino having a ar(lower)alkoxycarbonyl(lower)alkoxyimino, aminothiazolyl(lower)alkanoylamino having a carboxy(lower)alkoxyimino, or aminothiadiazolyl(lower)alkanoylamino having a lower alkoxyimino,
R² is ethynyl, and
R³ is carboxy or protected carboxy, and pharmaceutically acceptable salts thereof.

7. A compound of claim 6, wherein
R³ is carboxy, ar(lower)alkoxycarbonyl, or lower alkanoyloxy(lower)alkoxycarbonyl.

8. A compound of claim 7, wherein
R¹ is amino, formamido, phenylacetamido, aminothiazolylacetamido having methoxyimino, formamidothiazolylacetamido having methoxyimino, aminothiazolylacetamido having benzhydryloxycarbonylmethoxyimino, formamidothiazolylacetamido having benzhydryloxycarbonylmethoxyimino, aminothiazolylacetamido having carboxymethoxyimino, or aminothiadiazolylacetamido having ethoxyimino, and
R³ is carboxy, benzhydryloxycarbonyl, or pivaloyloxymethoxycarbonyl.

9. A compound of claim 8, which is
trifluoroacetic acid salt of 7-amino-3-ethynyl-3-cephem-4-carboxylic acid.

10. Syn isomer of a compound of claim 8, wherein
R¹ is 2-methoxyimino-2-(2-aminothiazol-4-yl)acetamido, 2-carboxymethoxyimino-2-(2-aminothiazol-4-yl)-acetamido, or 2-ethoxyimino-2-(5-amino-1,2,4-thiadiazol-3-yl)acetamido, and
R³ is carboxy.

11. A compound of claim 10, which is selected from the compound consisting of:
7-[2-ethoxyimino-2-(5-amino-1, 2, 4-thiadiazol-3-yl)acetamido]-3-ethynyl-3-cephem-4-carboxylic acid (syn isomer),
7-[2-carboxymethoxyimino-2-(2-aminothiazol-4-yl)acetamido]-3-ethynyl-3-cephem-4-carboxylic acid (syn isomer), and
7-[2-methoxyimino-2-(2-aminothiazol-4-yl)-acetamido]-3-ethynyl-3-cephem-4-carboxylic acid (syn isomer).

12. A pharmaceutical antimicrobial composition comprising an effective amount of a compound of claim 1 or pharmaceutically acceptable salt thereof in association with a pharmaceutically acceptable, substantially non-toxic carrier or excipient.

13. A method for producing a pharmaceutical antimicrobial composition which comprises mixing an effective amount of a compound of claim 1 or pharmaceutically acceptable salt thereof as an active ingredient with an inert carrier.

14. A method for treatment of infectious diseases in human beings and animals which comprises administering to the subject the antimicrobial composition of claim 12.

15. A pharmaceutical antimicrobial composition comprising an effective amount of a compound of claim 6 or pharmaceutically acceptable salt thereof in association with a pharmaceutically acceptable, substantially non-toxic carrier or excipient.

16. A method for producing a pharmaceutical antimicrobial composition which comprises mixing an effective amount of a compound of claim 6 or pharmaceutically acceptable salt thereof as an active ingredient with an inert carrier.

17. A method for treatment of infectious diseases in human beings and animals which comprises administering to the subject the antimicrobial composition of claim 15.

* * * * *